US006417325B1

(12) United States Patent
Blaschuk et al.

(10) Patent No.: US 6,417,325 B1
(45) Date of Patent: Jul. 9, 2002

(54) COMPOUNDS AND METHODS FOR CANCER THERAPY

(75) Inventors: Orest W. Blaschuk, Westmount; Barbara J. Gour, Kemptville; Riaz Farookhi, Montreal, all of (CA)

(73) Assignee: McGill University, Montreal (CA)

( * ) Notice: Subject to any disclaimer, the term of this patent is extended or adjusted under 35 U.S.C. 154(b) by 0 days.

(21) Appl. No.: 09/357,717

(22) Filed: Jul. 20, 1999

Related U.S. Application Data

(63) Continuation-in-part of application No. 09/248,074, filed on Feb. 10, 1999, which is a continuation-in-part of application No. 08/996,679, filed on Dec. 23, 1997, now Pat. No. 6,169,071, which is a continuation-in-part of application No. 08/893,534, filed on Jul. 11, 1997, now Pat. No. 6,031,072.
(60) Provisional application No. 60/021,612, filed on Jul. 12, 1996, now abandoned.

(51) Int. Cl.$^7$ ............................ A61R 38/00; C07K 5/00; C07K 7/00

(52) U.S. Cl. .................... 530/317; 530/300; 530/324; 530/328; 530/329; 530/327; 514/9; 514/12; 514/15; 514/16; 514/17; 424/185.1

(58) Field of Search .................................. 530/317, 300, 530/324, 327, 328, 329; 514/9, 12, 15, 16, 17; 424/185.1

(56) References Cited

U.S. PATENT DOCUMENTS

| | | | |
|---|---|---|---|
| 5,231,082 A | 7/1993 | Schasteen | 514/11 |
| 5,352,667 A | 10/1994 | Lider et al. | 514/19 |
| 5,510,628 A | 4/1996 | Georger, Jr. et al. | 257/32 |
| 5,585,351 A | 12/1996 | Ranscht | 514/12 |
| 5,591,432 A | 1/1997 | Bronson et al. | 424/130.1 |
| 5,646,250 A | 7/1997 | Suzuki | 530/350 |
| 5,665,590 A | 9/1997 | Yang | 435/6 |
| 6,031,072 A * | 2/2000 | Blaschuk | 530/317 |
| 6,169,071 B1 * | 1/2001 | Blaschuk | 514/15 |
| 6,207,639 B1 * | 3/2001 | Blaschuk | 514/11 |

FOREIGN PATENT DOCUMENTS

| | | |
|---|---|---|
| EP | 406 428 B1 | 1/1991 |
| WO | WO 91/04745 | 4/1991 |
| WO | WO 92/08731 | 5/1992 |
| WO | WO 94/11401 | 5/1994 |
| WO | WO 96/40781 | 12/1996 |
| WO | WO 97/07209 | 2/1997 |
| WO | WO 98/02452 | 1/1998 |
| WO | WO 98/45319 | 10/1998 |

OTHER PUBLICATIONS

Alexander et al., "An N–Cadherin–Like Protein Contributes to Solute Barrier Maintenance in Cultured Endothelium," *Journal of Cellular Physiology* 156: 610–618, 1993.

Ali et al., "Conformationally Constrained Peptides and Semipeptides Derived from RGD as Potent Inhibitors of the Platelet Fibrinogen Receptor and Platelet Aggregation," *J. Med. Chem.* 37(36): 769–780, 1994.

Beesley et al., "The post–synaptic density: putative involvement in synapse stabilization via cahderins and covalent modification by ubiquitination," *Biochemical Society Transactions23*: 59–64, 1995.

Blakemore, "Remyelination of CNS axons by Schwann cells transplanted from the sciatic nerve," *Nature* 266: 68–69, 1977.

Blaschuk and Farookhi, "Estradiol Stimulates Cadherin Expression in Rat Granulosa Cells," *Developmental Biology* 136: 564–567, 1989.

Blaschuk et al., "E–Cadherin, estrogens and cancer: is there a connection?" *The Canadian Journal of Oncology* 4(4): 291–301, 1994.

Blaschuck et al., "Identification of a Conserved Region Common to Cadherins and Influenza Strain A Hemagglutinins," *Proc.Natl. Acad. Sci. USA* 76(1): 514–517, 1979.

Byers et al., "Fibroblast Growth Factor Receptors Contain a Conserved HAV Region Common to Cadherins and Influenza Strain A Hemagglutinins: A Role in Protein–Protein Interactions?," *Development Biology* 152: 411–414, 1992.

Cardarelli et al., "The Collagen Receptor α2β1, from MG–63 and HT1080 Cells, Interacts with a Cyclic RGD Peptide," *The Journal of Biological Chemisty* 267(23): 23159–23164, 1992.

Craig et al., "Concept and Progress in the Development of RGD–Containing Peptide Pharmaceuticals" *Biopolymers (Peptide Science)* 37: 157–175, 1991.

Doherty and Walsh, "Signal transduction events underlying neurite outgrowth stimulated by cell adhesion molecules," *Current Opinion in Neurobiology* 4: 49–55, 1994.

Letourneau et al., "Interactions of Schwann Cells with neurites and with Other Schwann Cells Involve the Calcium–dependent Adhesion Molecule, N–cadherin," *Journal of Neurobiology* 22(7): 707–720, 1991.

Lutz et al.,"Secondary Structure of the HAV Peptide Which Regulates Cadherin–Cadherin Interaction," *Journal of Biomolecular Structure & Dynamics* 13(3): 447–455, 1995.

Munro and Balschuk, Cell Adhesion and Invasion in Cancer Metastasis, R.G. Landes Company, Austin, TX. 1996, Chapter 3, "The Structure, Function and Regulation of Cadherins," pp. 17–34.

(List continued on next page.)

Primary Examiner—Avis M. Davenport
(74) Attorney, Agent, or Firm—SEED Intellectual Property Law Group PLLC

(57) ABSTRACT

Agents that inhibit the development of cancer and tumor growth are provided. Such agents comprise a classical cadherin CAR sequence HAV within a cyclic peptide ring, and may be used to prevent or treat cancer.

Newton et al., "N–Cadherin Mediates Sertoli Cell–Spermatogenic Cell Adhesion," *Developmental Dynamics* 197: 1–13, 1993.

7 Claims, 28 Drawing Sheets-

OTHER PUBLICATIONS

Overduin et al., "Solution Structure of the Epithelial Cadherin Domain Responsible for Selective Cell Adhesion," *Science 267*: 386–389, 1995.

Redies and Takeichi, "Cadherins in the Developing Central Nervous System: An Adhesive Code for Segmental and Functional Subdivisions," *Developmental Biology 180*: 413–423, 1996.

Samanen et al., "Development of a Small RGD Peptide Fibrinogen Receptor Antagonist with Potent Antiaggregatory Activity in Vitro," *J. Med. Chem. 34*(10): 3114–3125, 1991.

Shapiro et al., "Structural basis of cell–cell adhesion by cadherins," *Nature 374*: 327–337, 1995.

Willems et al., "Cadherin–dependent cell aggregation is affected by decapeptide derived from rat extracellular super–oxide dismutase," *FEBS Letters 363*: 289–292, 1995.

Williams et al., "The Priamary Structure of Hen Ovotransferrin," *Eur. J. Biochem. 122*: 297–303, 1982.

Blakemore, "Remyelination of CNS axons by Schwann cells transplated from the sciatic nerve, "*Nature 266*: 68–69, 1977.

Blaschuk et al., "E–Cadherin, estrogens and cancer: is there is a connection' " *The Canadian Journal of Oncology 4*(4): 291–301, 1994.

Bottenstein and Sato, "Growth of a rat neuroblastoma cell line in serum–free supplemented medium, " *Proc. Natl. Acad. Sci. USA 76*(1): 514–517, 1979.

Brecknell et al., "Bridge grafts of Fibroblast Growth Factor–4–Secreting Schwannonoma Cells Promote Functional Axonal Regeneration in the Nigorstriatal Pathway of the Adult Rat, " *Neuroscience 74*(3): 775–784, 1996.

Brockes et al., "Studies on Cultured Rat Schwann Cells. I. Establishment of Purified Populations from Cultures of Peripheral Nerve, " *Brain Research 165*: 105–118, 1979.

Brook et al., "Morphology and Migration of Cultured Schwann Cell Transplanted Into the Fimbria and Hippocampus in Adult Rats, " *GLIA 9*: 292–304, 1993.

Carlstedt et al., "Nerve Fibre Regeneration Across the PNS–CNS Interface at the Root–Spinal Cord Junction," *Brain Research Bulletin 22*: 93–102, 1989.

Cepek et al., "Expression of a candidate cadherin in T lymphocytes, " *Proc. Natl. Acad. Sci. USA 93*:6567–6571, 1996.

Chuah et al., "Differentiation and survival of rat olfactory epithelial neurons in dissociated cell culture, " *Developmental Brain Research 60*: 123–132, 1991.

Doherty and Walsh, "CAM–FGF Receptor Interactions: A Model for Axonal Growth," *Molecular and Cellular Neuroscience 8*(Article No. 0049): 99–111, 1996.

Doherty et al., "Neurite Outgrowth in Response to Transfected N–CAM and N–Cadherin Reveals Fundamental Differences in Neuronal Responsiveness to CAMS, " *Neuron 6*: 247–258, 1991.

Duncan et al., "Transplantation of oligdendrocytes and Schwann cells into the spinal cord of the myelin–deficient rat, " *Journal of Neurocytology 17*: 351–360, 1988.

Fok–Seang et al., "An analysis of astrocytic cell lines with different abilities to promote axon growth, " *Brain Research 689*: 207–223, 1995.

Fok–Seang et al., "Migration of Oligodendrocyte Precursors on Astrocytes and Meningeal Cells, " *Developmental Biology 171*: 1–15, 1995.

Franz, "Percutaneous Absorption. On The Relevance Of In Vito Data, " *The Journal of Investigative Dermatology 64*(3): 190–195, 1975.

Franz, "The Finite Dose Technique as a Valid *in Vitro* Model for the Study of Percutaneous Absorption in Man, " *Curr. Probl. Dermatol. 7*: 58–68, 1978.

Ghirnikar and Eng, "Astrocyte–Schwann Cell Interactions in Culture, " *GLIA 11*: 367–377, 1994.

Gumbiner et al., "The Role of the Cell Adhesion Molecule Uvomorulin in the Formation and Maintenence of the Epithelial Junctional Complex, " *The Journal of Cell Biology 107*: 1575–1587, 1988.

Iruela–Arispe et al., "Expression of SPARC during Development of the Chicken Choriallantoic Membrane: Evidence for Regulated Proteolysis In Vivo, " *Molecular Biology of the Cell 6*: 327–343, 1995.

Laird et al., "Gap Junction Turnover, Intracellular Trafficking, anf Phosphorylation of Connexin43 in Brefeldon A–treated Rat Mammary Tumor Cells, " *The Journal of Cell Biology 131*(5): 1193–1203, 1995.

Lee et al., "Expression of the Homotypic Adhesion Molecule E–Cadherin by Immature Murine Thymocytes and Thymic Epithelial Cells, " *Journal of Immunology 152*: 5653–5659, 1994.

Liuzzi and Lasek, "Astrocytes Block Axonal Regeneration in Mammals by Activating the Physiological Stop Pathway," *Science 237*: 642–645, 1987.

Matsuzaki et al., "cDNAs of Cell Adhesion Molecules of Different Specificity Induce Changes in Cell Shape and Border Formation in Cultured S180 Cells, " *The Journal of Cell Biology 110*: 1239–1252, 1990.

McCarthy and Vellis, "Preparation of Seperate Astroglial and Oligodendroglial Cell Cultures from Rat Cerebral Tissue, " *J. Cell Biology 85*: 890–902, 1980.

Mege et al., "Construction of epithelioid sheets by transfection of mouse sarcoma cells with cDNAS for chicken cell adhesion molecules, " *Proc. Natl. Acad. Sci. USA 85*: 7274–7278, 1988.

Moran, "The Protein Delivery Service. Advances in technologies for delivering proteins and peptides in therapeutically useful foms, " *Pharmaceutical Forumm Issue 6*: 4–7, 1996.

Munro et al., "Characterization of Cadherins Expressed by Murine Thymocytes, " *Cellular Immunology 169*(Article No. 0123): 309–312, 1996.

Nose et al., "Localization of Specificity Determining Sites in Cadherin Cell Adhesion Molecules, " *Cell 61*: 147–155, 1990.

Orr, "Angiogenesis Research Offers New Approaches to Treatment of Disease, " *Genetic Engineering News*, pp. 15–16, 42, May 1, 1996.

Saffell et al., "Expression of a Dominant Negative FGF Receptor Inhibits Axonal Growth and FGF Receptor Phosphorylation Stimulated by CAMs, " *Neuron*, pp. 231–242, Feb. 1997.

Tsutsui et al., "Expression of Cadherin–Catenin Complexes in Human Leukemia Cell Lines, " *J. Biochem. 120*: 1034–1039, 1996.

Wickelgren, "Breaking the Skin Barrier, " *PS 12*: 86–88, 1996.

Williams et al., "Activation of the FGF Receptor Underlies Neurite Outgrowth Stimulated by L1, N–CAM, and N–Cadherin, " *Neuron 13*: 583–594, 1994.

\* cited by examiner

```
human N-cad   DWVIPPINLPENSRGPFPQELVRIRSDRDKNLSLRYSVTGPGADQPPTGIFILNPISGQLSVTKPLDREQ
mouse N-cad   DWVIPPINLPENSRGPFPQELVRIRSDRDKNLSLRYSVTGPGADQPPTGIFILNPISGQLSVTKPLDREL
cow N-cad     DWVIPPINLPENSRGPFPQELVRIRSDRDKNLSLRYSVTGPGADQPPTGIFIINPISGQLSVTKPLDREL
human P-cad   DWVAPISVPENGKGPFPQRLNQLKSNKDRDTKIFYSITGPGADSPPEGVFAVEKETGWLLLNKPLDREE
mouse P-cad   EWVMPPIFVPENGKGPFPQRLNQLKSNKDRGTKIFYSITGPGADSPPEGVFTIEKESGWLLLHMPLDREK
human E-cad   DWVIPPISCPENEKGPFPKNLVQIKSNKDKEGKVFYSITGQGADTPPVGVFIIERETGWLKVTEPLDRER
mouse E-cad   DWVIPPISCPENEKGEFPKNLVQIKSNRDKETKVFYSITGQGADKPPVGVFIIERETGWLKVTQPLDREA human N-cad   IARFHLRAHAVDINGNQVENPIDIVINVIDMNDNRPEF
mouse N-cad   IARFHLRAHAVDINGNQVENPIDIVINVIDMNDNRPEF
cow N-cad     IARFHLRAHAVDINGNQVENPIDIVINVIDMNDNRPEF
human P-cad   IAKYELFGHAVSENGASVEDPMNISIIVTDQNDHKPKF
mouse P-cad   IVKYELYGHAVSENGASVEEPMNISIIVTDQNDNKPKF
human E-cad   IATYTLFSHAVSSNGNAVEDPMEILITVTDQNDNKPEF
mouse E-cad   IAKYILYSHAVSSNGEAVEDPMEIVITVTDQNDNRPEF
```

Fig. 2

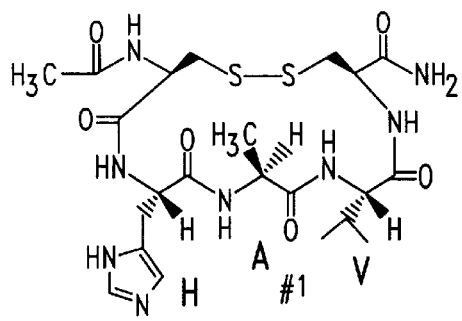
N-Ac-<u>CHAVC</u>-NH₂
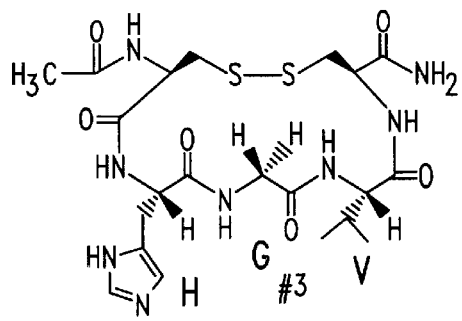
N-Ac-<u>CHGVC</u>-NH₂
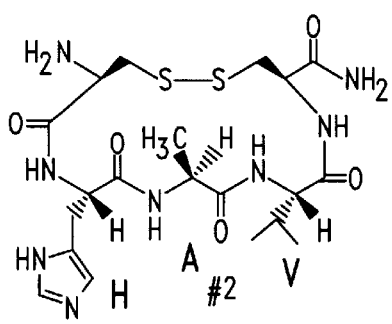
H-<u>CHAVC</u>-NH₂
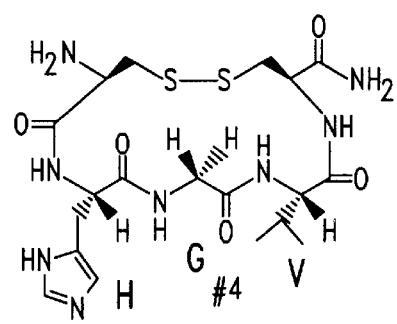
H-<u>CHGVC</u>-NH₂
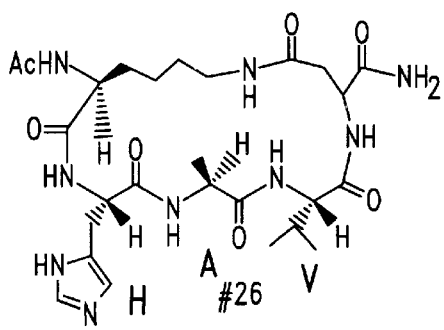
N-Ac-<u>KHAVD</u>-NH₂
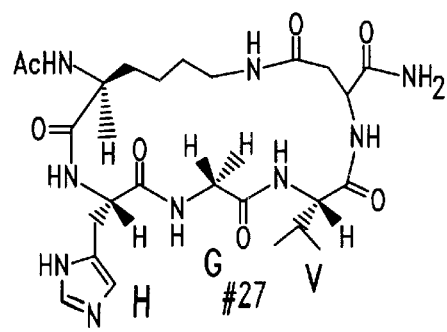
N-Ac-<u>KHGVD</u>-NH₂
*Fig. 3A*

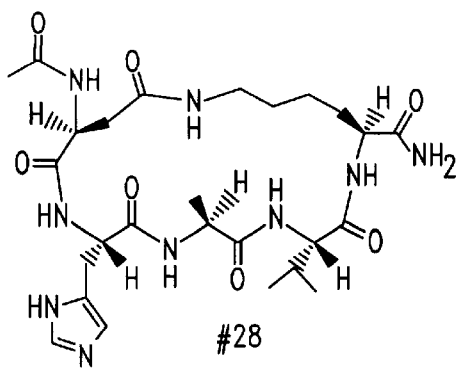
N-Ac-DHAVK-NH₂
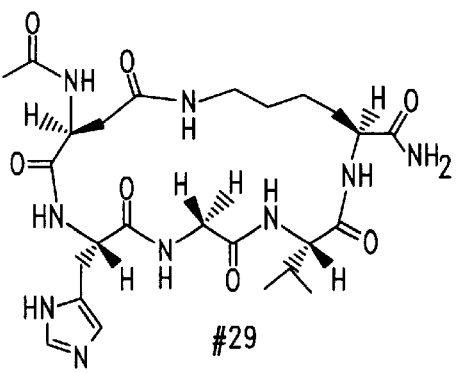
N-Ac-DHGVK-NH₂
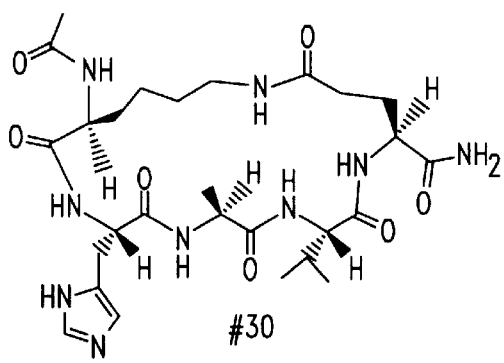
N-Ac-KHAVE-NH₂
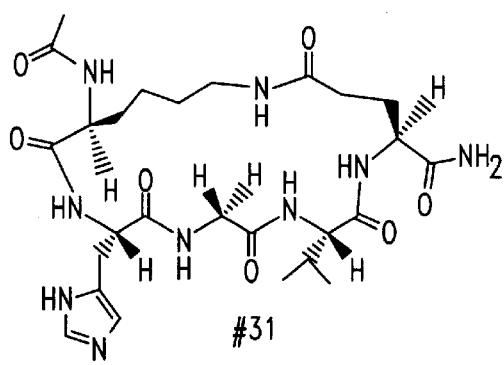
N-Ac-KHGVE-NH₂
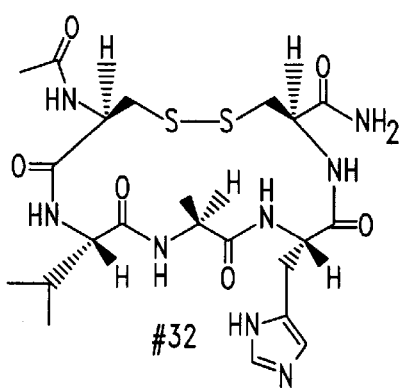
N-Ac-CVAHC-NH₂
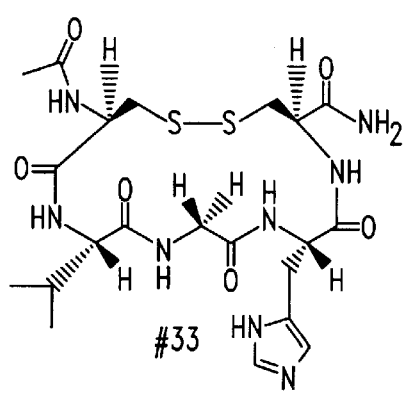
N-Ac-CVGHC-NH₂
*Fig. 3B*

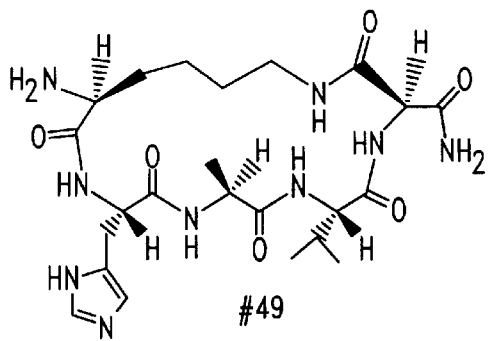
H-KHAVD-NH$_2$
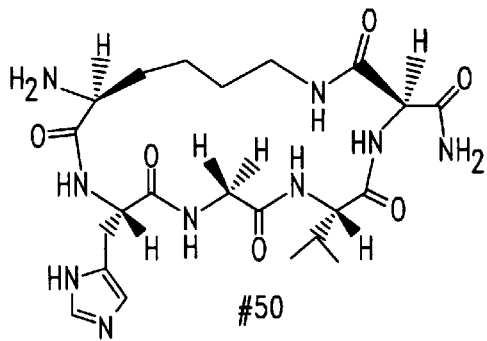
H-KHGVD-NH$_2$
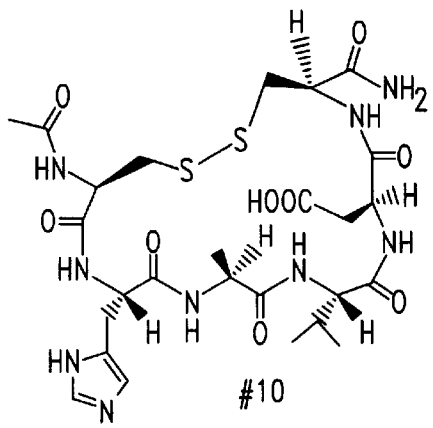
N-Ac-CHAVDC-NH$_2$
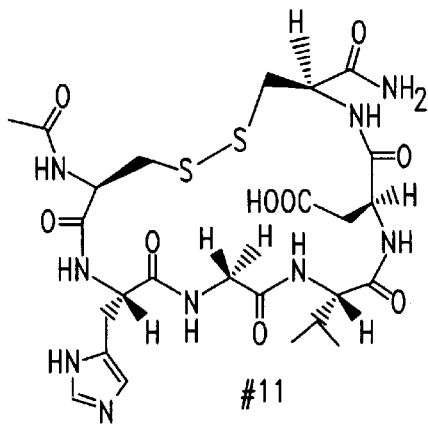
N-Ac-CHGVDC-NH$_2$
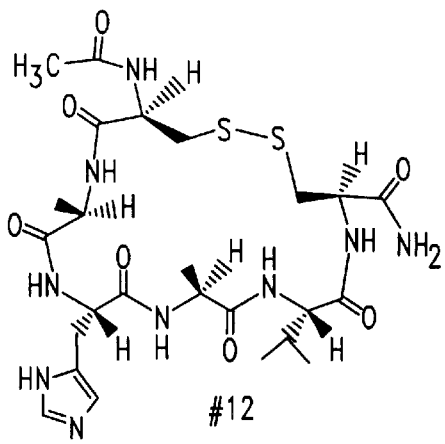
N-Ac-CAHAVC-NH$_2$
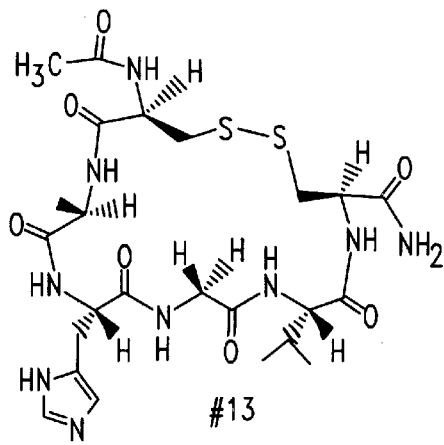
N-Ac-CAHGVC-NH$_2$
*Fig. 3C*

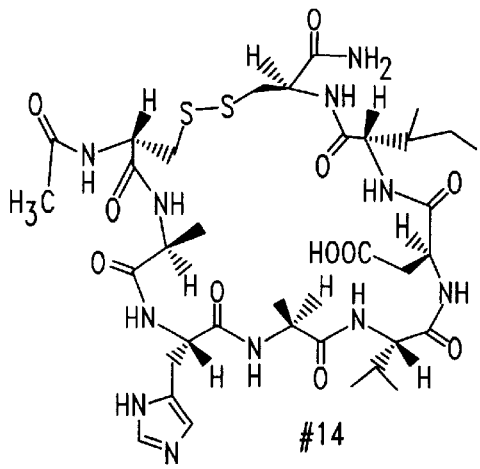
14
N-Ac-CAHAVDIC-NH₂
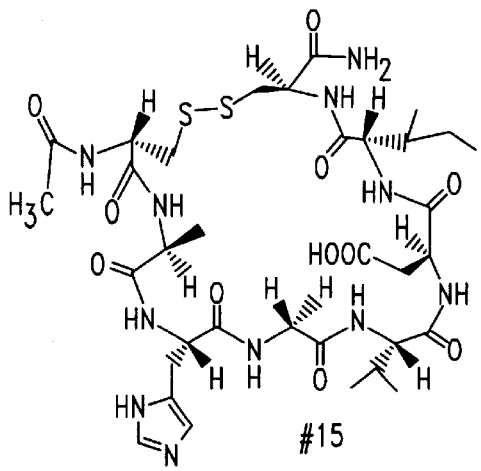
15
N-Ac-CAHGVDIC-NH₂
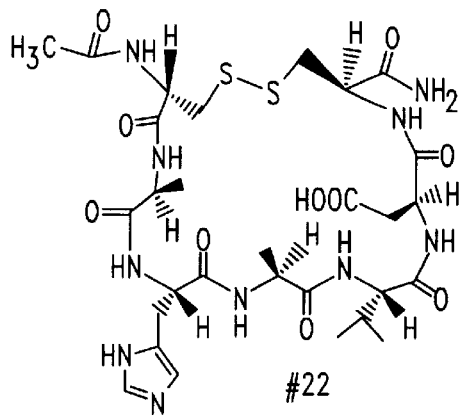
22
N-Ac-CAHAVDC-NH₂
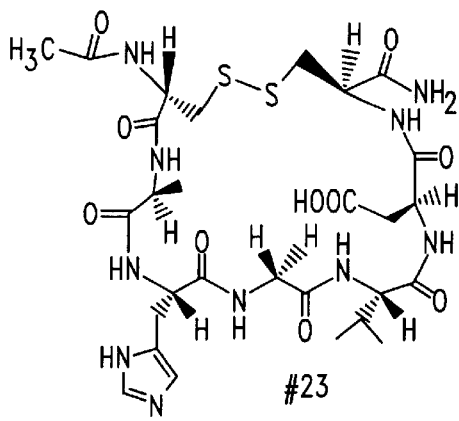
23
N-Ac-CAHGVDC-NH₂
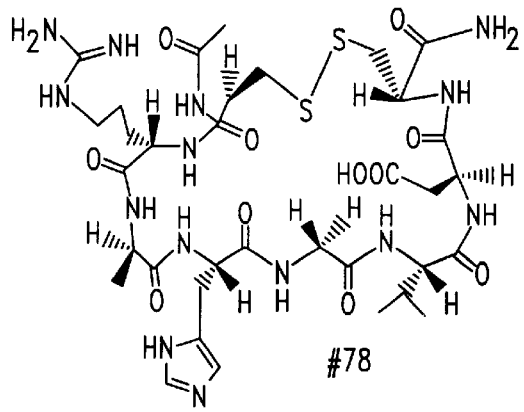
78
N-Ac-CRAHAVDC-NH₂
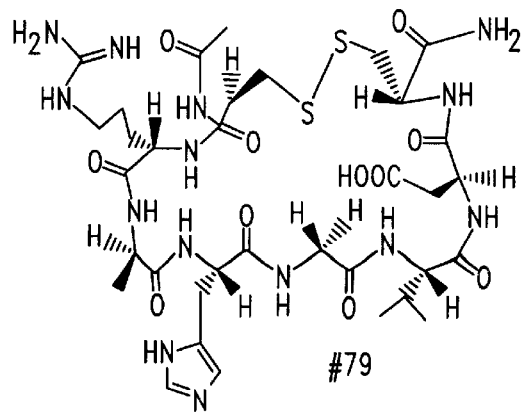
79
N-Ac-CRAHGVDC-NH₂
Fig. 3D

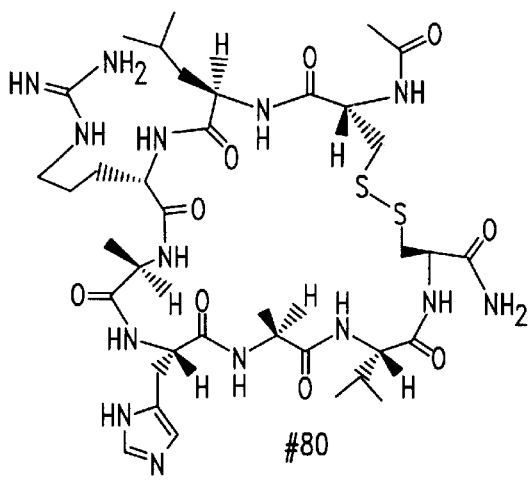
N-Ac-CLRAHAVC-NH₂
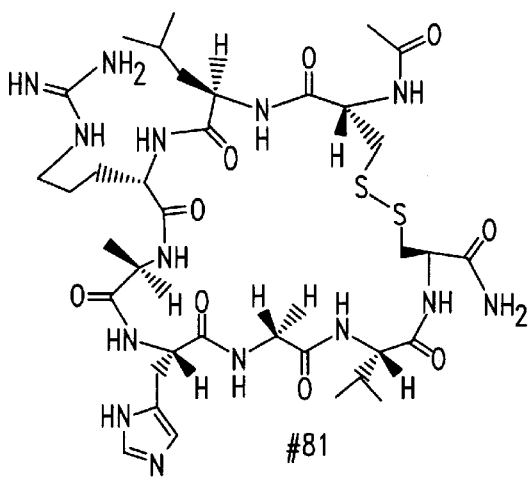
N-Ac-CLRAHGVC-NH₂
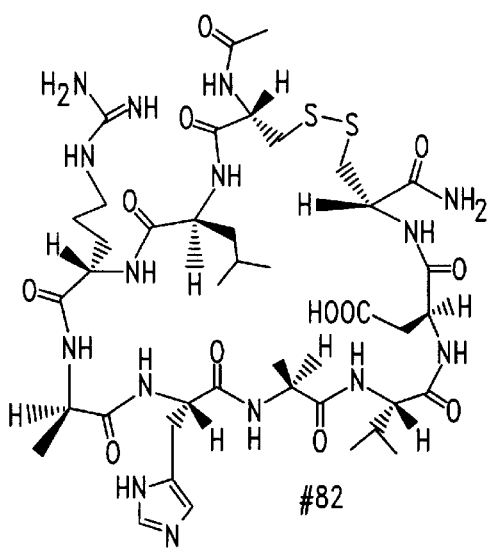
N-Ac-CLRAHAVDC-NH₂
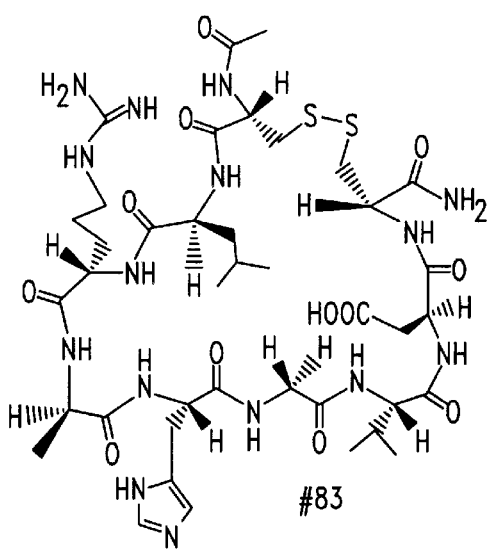
N-Ac-CLRAHGVDC-NH₂
Fig. 3E

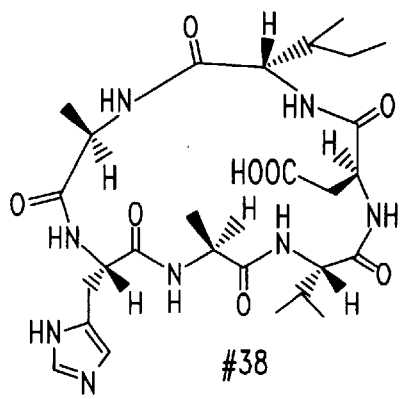
AHAVDI
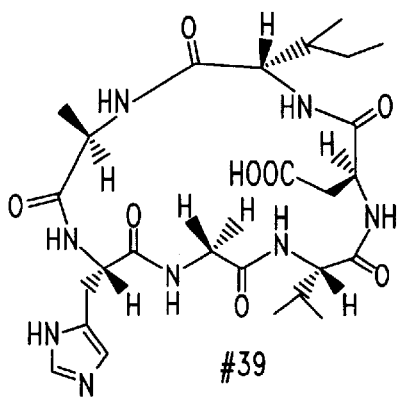
AHGVDI
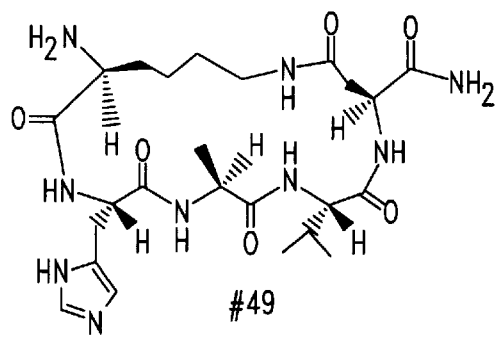
H-KHAVD-NH$_2$
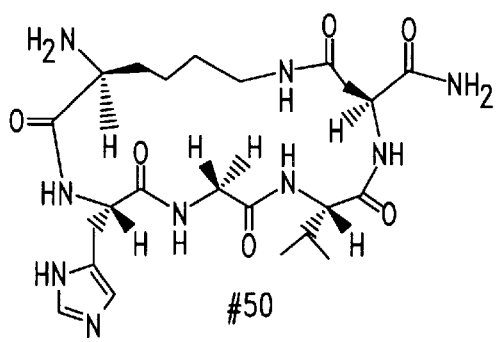
H-KHGVD-NH$_2$
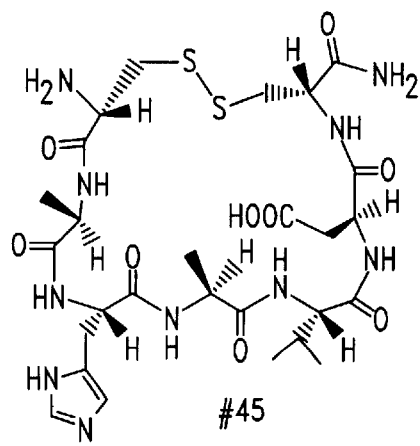
H-CAHAVDC-NH$_2$
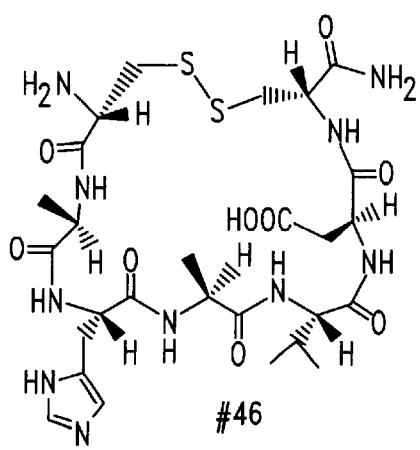
H-CAHGVDC-NH$_2$
*Fig. 3F*

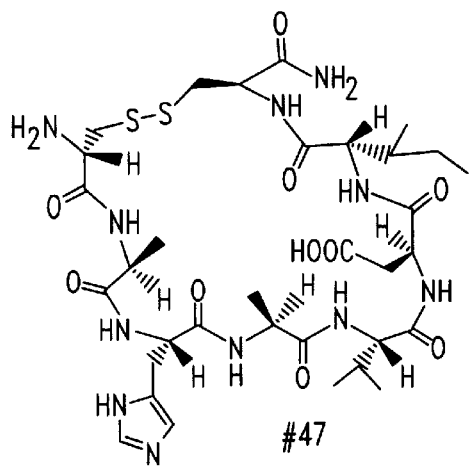
H-CAHAVDIC-NH2
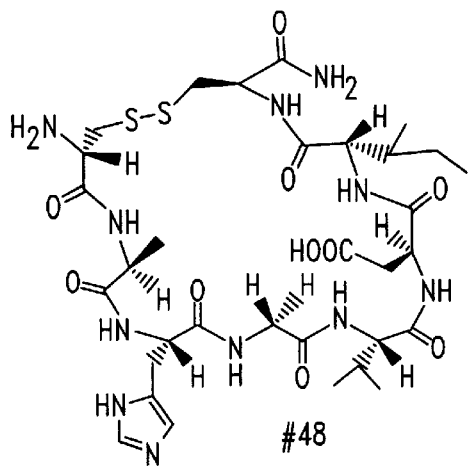
H-CAHGVDIC-NH2
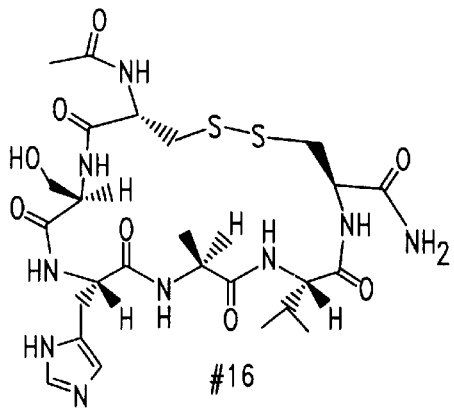
N-Ac-CSHAVC-NH2
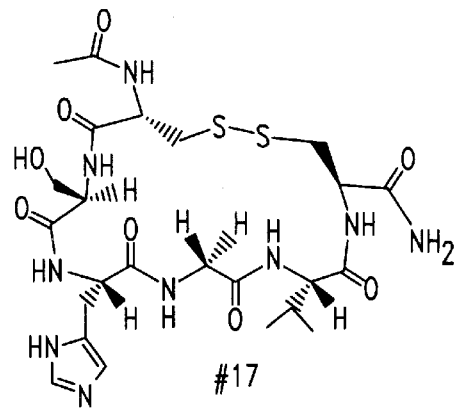
N-Ac-CSHGVC-NH2
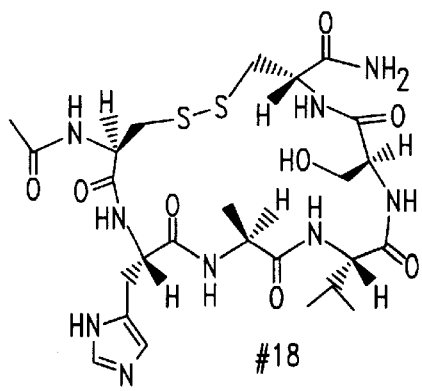
N-Ac-CHAVSC-NH2
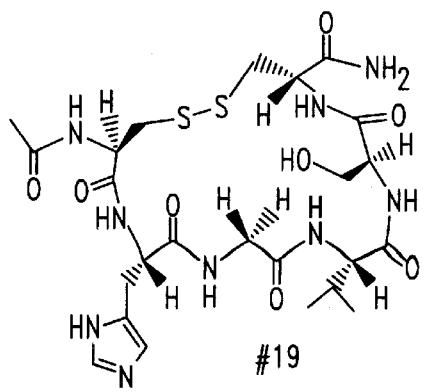
N-Ac-CHGVSC-NH2
Fig. 3G

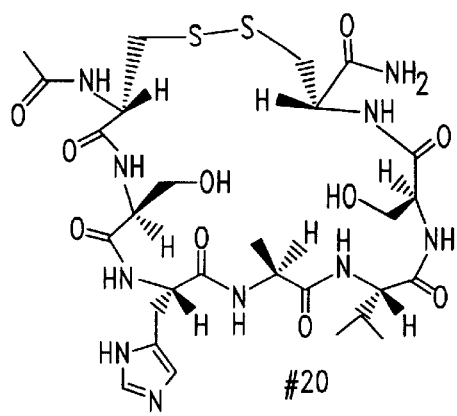
20
N-Ac-CSHAVSC-NH₂
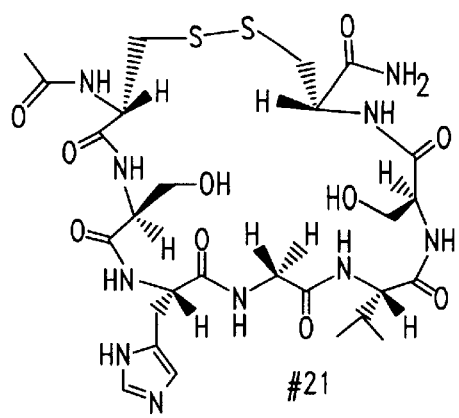
21
N-Ac-CSHGVSC-NH₂
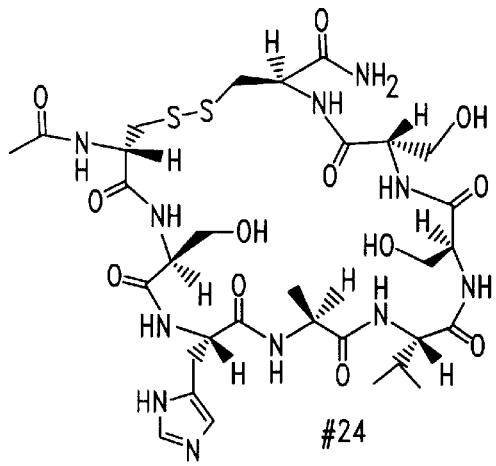
24
N-Ac-CSHAVSSC-NH₂
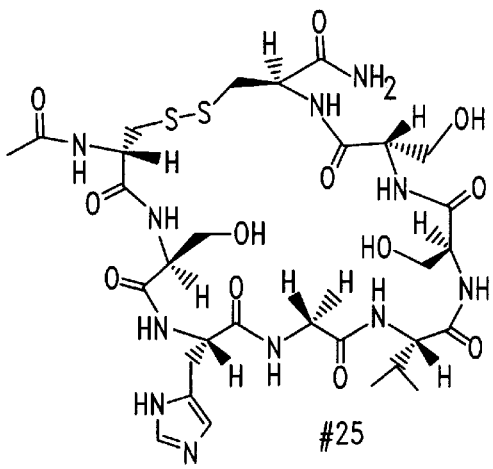
25
N-Ac-CSHGVSSC-NH₂
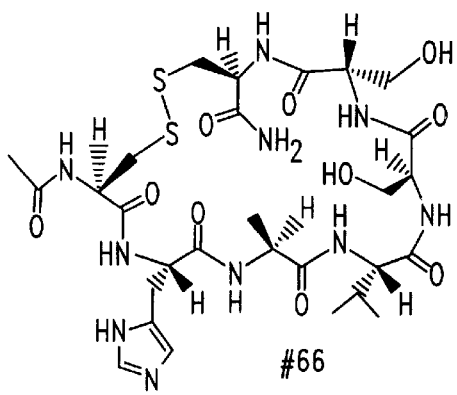
66
N-Ac-CHAVSSC-NH₂
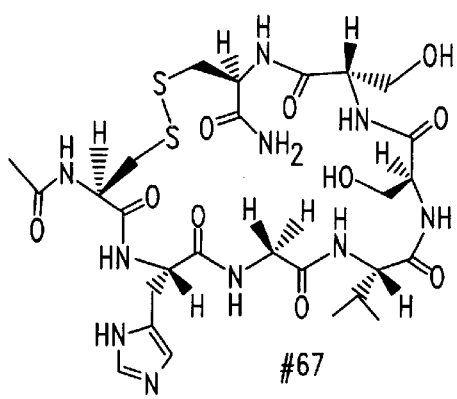
67
N-Ac-CHGVSSC-NH₂
Fig. 3H

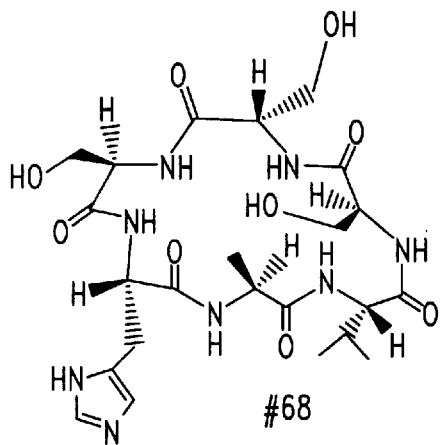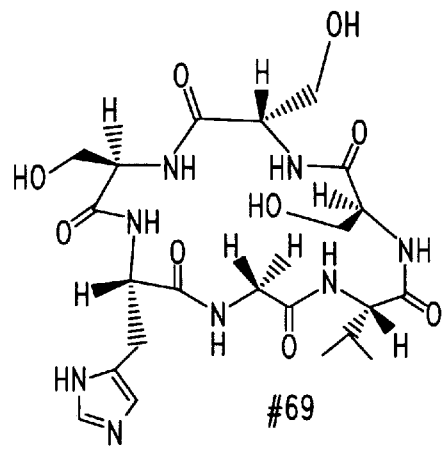
SHAVSS  SHGVSS
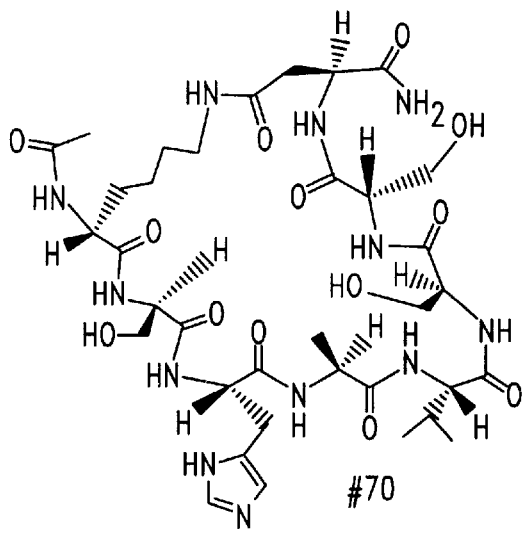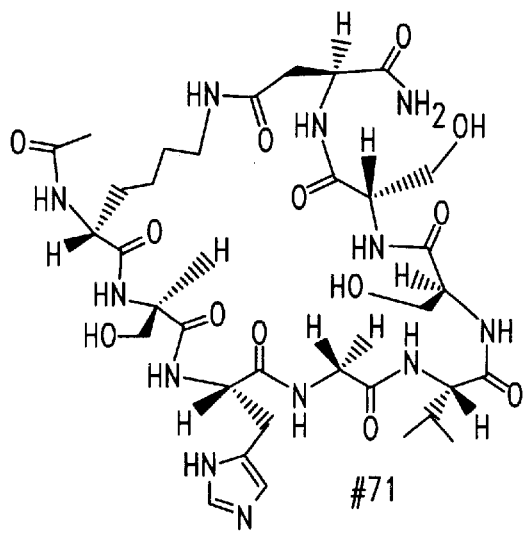
N-Ac-KSHAVSSD-NH$_2$  N-Ac-KSHGVSSD-NH$_2$
Fig. 31

COMPOUNDS AND METHODS FOR CANCER THERAPY

CROSS-REFERENCE TO RELATED APPLICATIONS

This application is a continuation-in-part of U.S. Ser. No. 09/248,074, filed Feb. 10, 1999, which is a continuation-in-part of U.S. Ser. No. 08/996,679, filed Dec. 23, 1997, now issued as U.S. Pat. No. 6,169,071, which is a continuation in part of U.S. Ser. No. 08/893,534, filed Jul. 11, 1997, now issued as U.S. Pat. No. 6,031,072, which claims the benefit of U.S. Provisional Application No. 60/021,612, filed on Jul. 12, 1996 now abandoned.

TECHNICAL FIELD

The present invention relates generally to methods for modulating cell adhesion, and more particularly to cyclic peptides comprising a classical cadherin cell adhesion recognition sequence, and to the use of such cyclic peptides for cancer therapy.

BACKGROUND OF THE INVENTION

Cancer is a significant health problem throughout the world. Although advances have been made in detection and therapy of cancer, no universally successful method for prevention or treatment is currently available. Cancer therapy currently relies on a combination of early diagnosis and aggressive treatment, which may include radiotherapy, chemotherapy or hormone therapy. However, the toxicity of such treatments limits the use of presently available anti-cancer agents. The high mortality rate for many cancers indicates that improvements are needed in cancer prevention and treatment.

Cell adhesion is a complex process that is important for tumor growth. Cell adhesion is mediated by specific cell surface adhesion molecules (CAMs). There are many different families of CAMs, including the immunoglobulin, integrin, selectin and cadherin superfamilies, and each cell type expresses a unique combination of these molecules. Cadherins are a rapidly expanding family of calcium-dependent CAMs (Munro et al., In: *Cell Adhesion and Invasion in Cancer Metastasis*, P. Brodt, ed., pp. 17–34, RG Landes Co.(Austin Tex., 1996). The classical cadherins (abbreviated CADs) are integral membrane glycoproteins that generally promote cell adhesion through homophilic interactions (a CAD on the surface of one cell binds to an identical CAD on the surface of another cell), although CADs also appear to be capable of forming heterotypic complexes with one another under certain circumstances and with lower affinity. Cadherins have been shown to regulate epithelial, endothelial, neural and cancer cell adhesion, with different CADs expressed on different cell types. N (neural)—cadherin is predominantly expressed by neural cells, endothelial cells and a variety of cancer cell types. E (epithelial)—cadherin is predominantly expressed by epithelial cells. Other CADs are P (placental)—cadherin, which is found in human skin and R (retinal)—cadherin. A detailed discussion of the classical cadherins is provided in Munro SB et al., 1996, In: *Cell Adhesion and Invasion in Cancer Metastasis*, P. Brodt, ed., pp.17–34 (RG Landes Company, Austin Tex.).

The structures of the CADs are generally similar. As illustrated in FIG. 1, CADs are composed of five extracellular domains (EC1–EC5), a single hydrophobic domain (TM) that transverses the plasma membrane (PM), and two cytoplasmic domains (CP1 and CP2). The calcium binding motifs DXNDN (SEQ ID NO:8), DXD and LDRE (SEQ ID NO:9) are interspersed throughout the extracellular domains. The first extracellular domain (EC1) contains the classical cadherin cell adhesion recognition (CAR) sequence, HAV (His-Ala-Val), along with flanking sequences on either side of the CAR sequence that may play a role in conferring specificity. Synthetic peptides containing the CAR sequence and antibodies directed against the CAR sequence have been shown to inhibit CAD-dependent processes (Munro et al., supra; Blaschuk et al., *J. Mol. Biol.* 211:679–82, 1990; Blaschuk et al., *Develop. Biol.* 139:227–29, 1990; Alexander et al., *J Cell. Physiol.* 156:610–18, 1993). The three-dimensional solution and crystal structures of the EC1 domain have been determined (Overduin et al., *Science* 267:386–389, 1995; Shapiro et al., *Nature* 374:327–337, 1995).

Interactions between cell adhesion molecules, such as classical cadherins, are responsible for binding of tumor cells to one another, as well as for angiogenesis (i.e., the growth of blood vessels from pre-existing blood vessels). Cancer tumors are solid masses of cells, growing out of control, which require nourishment via blood vessels, and the formation of new capillaries is a prerequisite for tumor growth and the emergence of metastases. Inhibition of undesirable cell adhesion mediated by classical cadherins has the potential to provide new therapeutic approaches for cancer therapy. However, to date, no such therapies are available.

Accordingly, there is a need in the art for improved cancer therapeutic agents that inhibit tumor growth by either modulating adhesion of cancer cells, or modulating the adhesion between the endothelial cells of both newly formed and pre-existing tumor blood vessels. The present invention fulfills this need and further provides other related advantages.

SUMMARY OF THE INVENTION

The present invention provides cyclic peptides and methods for modulating cadherin-mediated cell adhesion. Within one aspect, the present invention provides modulating agents that inhibit cadherin-mediated cell adhesion. Such agents comprise the sequence His-Ala-Val within a cyclic peptide ring. Within one embodiment a modulating agent comprises a cyclic peptide having the formula:

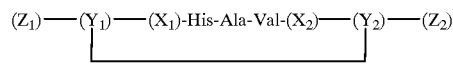

wherein $X_1$, and $X_2$ are optional, and if present, are independently selected from the group consisting of amino acid residues and combinations thereof in which the residues are linked by peptide bonds, and wherein $X_1$ and $X_2$ independently range in size from 0 to 10 residues, such that the sum of residues contained within $X_1$ and $X_2$ ranges from 1 to 12; wherein $Y_1$ and $Y_2$ are independently selected from the group consisting of amino acid residues, and wherein a covalent bond is formed between residues $Y_1$ and $Y_2$; and wherein $Z_1$ and $Z_2$ are optional, and if present, are independently selected from the group consisting of amino acid residues and combinations thereof in which the residues are linked by peptide bonds. Such cyclic peptides may comprise modifications such as an N-acetyl or N-alkoxybenzyl group and/or a C-terminal amide or ester group. Cyclic peptides may be cyclized via, for example, a disulfide bond; an amide bond between terminal functional groups, between residue side-chains or between one terminal functional group and one residue side chain; a thioether bond or $\delta_1\delta_1$-ditryptophan, or a derivative thereof.

Certain modulating agents comprise a cyclic peptide having the formula:

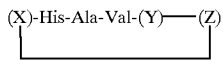

wherein Y is optional and, if present is selected from the group consisting of amino acid residues and combinations thereof in which the residues are linked by peptide bonds, and wherein Y ranges in size from 0 to 10 residues; and wherein X and Z are independently selected from the group consisting of amino acid residues, wherein a disulfide bond is formed between residues X and Z; and wherein X comprises an N-acetyl group.

Within specific embodiments, modulating agents as described above may be linked to a targeting agent and/or a drug. In addition, or alternatively, a modulating agent may further comprise one or more of: (a) a cell adhesion recognition sequence that is bound by an adhesion molecule other than a cadherin, wherein the cell adhesion recognition sequence is separated from any HAV sequence(s) by a linker; and/or (b) an antibody or antigen-binding fragment thereof that specifically binds to a cell adhesion recognition sequence bound by an adhesion molecule other than a cadherin.

The present invention further provides pharmaceutical compositions comprising a cell adhesion modulating agent as described above, in combination with a pharmaceutically acceptable carrier. Such compositions may further comprise a drug. Alternatively, or in addition, such compositions may comprise: (a) a peptide comprising a cell adhesion recognition sequence that is bound by an adhesion molecule other than a cadherin; and/or (b) an antibody or antigen-binding fragment thereof that specifically binds to a cell adhesion recognition sequence bound by an adhesion molecule other than a cadherin.

Within further aspects, methods for treating cancer and/or inhibiting metastasis of tumor cells in a mammal are provided, comprising administering to a mammal afflicted with cancer a cell adhesion modulating agent as described above.

Within related aspects, methods are provided for decreasing the size of a tumor in a mammal, comprising administering to a mammal having a tumor a cell adhesion modulating agent as described above.

These and other aspects of the invention will become evident upon reference to the following detailed description and attached drawings. All references disclosed herein are hereby incorporated by reference in their entirety as if each were individually noted for incorporation.

BRIEF DESCRIPTION OF THE DRAWINGS

FIG. 2 provides the amino acid sequences of mammalian classical cadherin EC1 domains: human N-cadherin (SEQ ID NO:1), mouse N-cadherin (SEQ ID NO:2), cow N-cadherin (SEQ ID NO:3), human P-cadherin (SEQ ID NO:4), mouse P-cadherin (SEQ ID NO:5), human E-cadherin (SEQ ID NO:6) and mouse E-cadherin (SEQ ID NO:7).

FIGS. 3A–3I provide the structures of representative cyclic peptides of the present invention (structures on the left hand side), along with similar, but inactive, structures (on the right).

FIG. 4A shows the cells 24 hours after being cultured in the presence of 500 µg/mL N-Ac-CHAVC-NH$_2$ (10× magnification; SEQ ID NO:10). FIG. 4B shows the cells (10× magnification) 24 hours after being cultured in the presence of the control peptide N-Ac-CHGVC-NH$_2$ (SEQ ID NO:11). FIG. 4C shows the cells (10× magnification) in the absence of cyclic peptide. FIGS. 4D–F show the cells (20× magnification) 48 hours after exposure to N-Ac-CHAVC-NH$_2$ (SEQ ID NO:10) at concentrations of 1 mg/mL, 100 µg/mL and 10 µg/mL, respectively. Note that the SKOV3 cells retract from one another and round-up when cultured in the presence of N-Ac-CHAVC-NH$_2$ (SEQ ID NO:10).

FIG. 6A shows the cells 24 hours after being cultured in the presence of 1 mg/ml of N-Ac-CHAVSC-NH$_2$ (SEQ ID NO:25). FIG. 6B shows the cells 24 hours after being cultured in the presence of 100 µg/ml of N-Ac-CHAVSC-NH$_2$ (SEQ ID NO:25). FIG. 6C shows the cells 24 hours after being cultured in the presence of 10 µg/ml of N-Ac-CHAVSC-NH$_2$ (SEQ ID NO:25). Note that the cells retract form one another in the presence of 100 µg/ml of N-Ac-CHAVSC-NH$_2$ (SEQ ID NO:25), whereas they round up in the presence of 1 mg/ml of this peptide.

FIG. 7B shows the cells 48 hours after being cultured in the presence of 500 µg/ml of N-Ac-CHAVC-NH$_2$ (SEQ ID NO:10). FIG. 7A shows untreated cultures of human melanoma ME115 cells. Note that N-cadherin is localized in intracellular vesicles in cells treated with peptide, whereas it is present at the surface in the untreated cells.

FIG. 8B shows the cells 48 hours after being cultured in the presence of 500 µg/ml of N-Ac-CHAVC-NH$_2$ (SEQ ID NO:10). FIG. 8A shows untreated monolayer cultures of A1N4 human breast epithelial cells. Note that the distribution of E-cadherin is non-contiguous in cells treated with the cyclic peptide. Furthermore, gaps have appeared in the monolayer of cells treated with the peptide.

FIGS. 18A and 18B show SKOV3 cells treated for 48 hours with the control peptide N-Ac-CHGVC-NH$_2$ (SEQ ID NO:11) at a concentration of 0.5 mg/mL (FIG. 18A) or 0.25 mg/mL (FIG. 18B). FIGS. 18C and 18D show SKOV3 cells treated for 48 hours with N-Ac-CHAVC-NH$_2$ (SEQ ID NO:10) at a concentration of 0.5 mg/mL (FIG. 18C) or 0.25 mg/mL (FIG. 18D). The fluorescent green nuclei in FIGS. 18C and 18D indicate cell death.

DETAILED DESCRIPTION OF THE INVENTION

Figure 1:
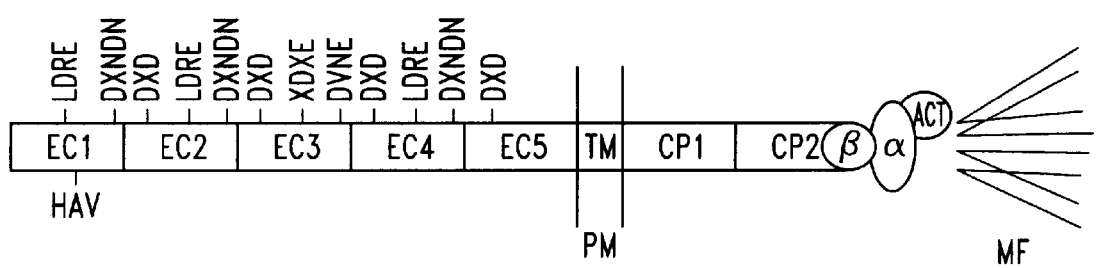
FIG. 1 is a diagram depicting the structure of classical CADs. The five extracellular domains are designated EC1–EC5, the hydrophobic domain that transverses the plasma membrane (PM) is represented by TM, and the two cytoplasmic domains are represented by CP1 and CP2. The calcium binding motifs are shown by DXNDN (SEQ ID NO:8), DXD and LDRE (SEQ ID NO:9). The CAR sequence, HAV, is shown within EC1. Cytoplasmic proteins β-catenin (β), α-catenin (α) and α-actinin (ACT), which mediate the interaction between CADs and microfilaments (MF) are also shown.

As noted above, the present invention provides cell adhesion modulating agents comprising cyclic peptides that are capable of modulating cadherin-mediated processes, such as cell adhesion. In general, to modulate cadherin-mediated cell adhesion, a cadherin-expressing cell is contacted with a cell adhesion modulating agent (also referred to herein as a "modulating agent") either in vivo or in vitro. A modulating agent comprises a cyclic peptide that contains the classical cadherin cell adhesion recognition (CAR) sequence HAV (i.e., His-Ala-Val). Such modulating agents may further comprise one or more additional CAR sequences and/or an antibody (or antigen-binding fragment thereof) that specifically binds to a cadherin CAR sequence, as described below. Modulating agents generally inhibit adhesion of classical cadherin-expressing cells and may be used, for example, to treat diseases or other conditions characterized by undesirable cell adhesion.

Cell Adhesion Modulating Agents

The term "cell adhesion modulating agent," as used herein, refers to a molecule comprising at least one cyclic peptide that contains a cadherin cell adhesion recognition (CAR) sequence, generally HAV (His-Ala-Val). The term "cyclic peptide," as used herein, refers to a peptide or salt thereof that comprises (1) an intramolecular covalent bond between two non-adjacent residues and (2) at least one cadherin CAR sequence. The intramolecular bond may be a backbone to backbone, side-chain to backbone or side-chain to side-chain bond (i.e., terminal functional groups of a linear peptide and/or side chain functional groups of a terminal or interior residue may be linked to achieve cyclization). Preferred intramolecular bonds include, but are not limited to, disulfide, amide and thioether bonds. In addition to the cadherin CAR sequence HAV, a modulating agent may comprise additional CAR sequences, which may or may not be cadherin CAR sequences, and/or antibodies or fragments thereof that specifically recognize a CAR sequence. Additional CAR sequences may be present within the cyclic peptide containing the HAV sequence, within a separate cyclic peptide component of the modulating agent and/or in a non-cyclic portion of the modulating agent. Antibodies and antigen-binding fragments thereof are typically present in a non-cyclic portion of the modulating agent.

Within certain embodiments, a cyclic peptide preferably comprises an N-acetyl group (i.e., the amino group present on the amino terminal residue of the peptide prior to cyclization is acetylated). It has been found, within the context of the present invention, that the presence of such an acetyl group may enhance cyclic peptide activity for certain applications.

In addition to the CAR sequence(s), cyclic peptides generally comprise at least one additional residue, such that the size of the cyclic peptide ring ranges from 4 to about 15 residues, preferably from 5 to 10 residues. Such additional residue(s) may be present on the N-terminal and/or C-terminal side of a CAR sequence, and may be derived from sequences that flank the HAV sequence within one or more naturally occurring cadherins (e.g., N-cadherin, E-cadherin, P-cadherin, R-cadherin or other cadherins containing the HAV sequence) with or without amino acid substitutions and/or other modifications. Flanking sequences for endogenous N-, E-, P- and R-cadherin are shown in FIG. 2, and in SEQ ID NOs: 1 to 7. Database accession numbers for representative naturally occurring cadherins are as follows: human N-cadherin M34064, mouse N-cadherin M31131 and M22556, cow N-cadherin X53615, human P-cadherin X63629, mouse P-cadherin X06340, human E-cadherin Z13009, mouse E-cadherin X06115. Alternatively, additional residues present on one or both sides of the CAR sequence(s) may be unrelated to an endogenous sequence (e.g., residues that facilitate cyclization).

Preferred modulating agents include those that disrupt N-cadherin mediated cell adhesion. Such modulating agents may, for example, comprise a cyclic peptide such as N-Ac-CHAVC-NH$_2$ (SEQ ID NO:10), N-Ac-CHAVDC-NH$_2$ (SEQ ID NO:16), N-Ac-CHAVDIC-NH$_2$ (SEQ ID NO:31), N-Ac-CHAVDINC-NH$_2$ (SEQ ID NO:32), N-Ac-CHAVDINGC-NH$_2$ (SEQ ID NO:55), N-Ac-CAHAVC-NH$_2$ (SEQ ID NO:17), N-Ac-CAHAVDC-NH$_2$ (SEQ ID NO:19), N-Ac-CAHAVDIC-NH$_2$ (SEQ ID NO:18), N-Ac-CRAHAVDC (SEQ ID NO:20), N-Ac-CLRAHAVC-NH$_2$ (SEQ ID NO:21), N-Ac-CLRAHAVDC-NH$_2$ (SEQ ID NO:22), N-Ac-CSHAVC-NH$_2$ (SEQ ID NO:24), N-Ac-CHAVSC-NH$_2$ (SEQ ID NO:25), N-Ac-CSHAVSC-NH$_2$ (SEQ ID NO:26), N-Ac-CSHAVSSC-NH$_2$ (SEQ ID NO:27), N-Ac-CHAVSSC (SEQ ID NO:28), N-Ac-KHAVD-NH$_2$ (SEQ ID NO:12), N-Ac-DHAVK-NH$_2$ (SEQ ID NO:13), N-Ac-KHAVE-NH$_2$ (SEQ ID NO:14), N-Ac-AHAVDI-NH$_2$ (SEQ ID NO:23), N-Ac-SHAVDSS-NH$_2$ (SEQ ID NO:56), N-Ac-KSHAVSSD-NH$_2$ (SEQ ID NO:30) and derivatives thereof, including derivatives without the N-acetyl group.

Within certain preferred embodiments, as discussed below, relatively small cyclic peptides that do not contain significant sequences flanking the HAV sequence are preferred for modulating N-cadherin and E-cadherin mediated cell adhesion. Such peptides may contain an N-acetyl group and a C-amide group (e.g., the 5-residue ring N-Ac-CHAVC-NH$_2$ (SEQ ID NO:10) or N-Ac-KHAVD-$NH_2$ (SEQ ID NO:12)). The finding, within the present invention, that such relatively small cyclic peptides may be effective and all-purpose inhibitors of cell adhesion represents a unexpected discovery. Such cyclic peptides can be thought of as "master keys" that fit into peptide binding sites of each of the different classical cadherins, and are preferred for disrupting adhesion of certain cancer cells and endothelial cells. Small cyclic peptides may generally be used to specifically modulate cell adhesion by topical administration or by systemic administration, with or without linking a targeting agent to the peptide, as discussed below.

Within other preferred embodiments, a cyclic peptide may contain sequences that flank the HAV sequence on one or both sides that are designed to confer specificity for cell adhesion mediated by one or more specific cadherins, resulting in tissue and/or cell-type specificity. Suitable flanking sequences for conferring specificity include, but are not limited to, endogenous sequences present in one or more naturally occurring cadherins, and cyclic peptides having specificity may be identified using the representative screens provided herein. For example, it has been found, within the context of the present invention, that cyclic peptides that contain additional residues derived from the native E-cadherin sequence on the C-terminal side of the CAR sequence are specific for epithelial cells (i.e., such peptides disrupt E-cadherin mediated cell adhesion to a greater extent than they disrupt N-cadherin expression). The addition of appropriate endogenous sequences may similarly result in peptides that disrupt N-cadherin mediated cell adhesion. For example, it has been found within the context of the present invention, that cyclic peptides that contain additional residues derived from the native N-cadherin sequence on the C-terminal side of the CAR sequence are specific for N-cadherin expressing cells.

To facilitate the preparation of cyclic peptides having a desired specificity, nuclear magnetic resonance (NMR) and computational techniques may be used to determine the conformation of a peptide that confers a known specificity. NMR is widely used for structural analysis of molecules. Cross-peak intensities in nuclear Overhauser enhancement (NOE) spectra, coupling constants and chemical shifts depend on the conformation of a compound. NOE data provide the interproton distance between protons through space and across the ring of the cyclic peptide. This information may be used to facilitate calculation of the lowest energy conformation for the HAV sequence. Conformation may then be correlated with tissue specificity to permit the identification of peptides that are similarly tissue specific or have enhanced tissue specificity.

As noted above, multiple CAR sequences may be present within a modulating agent. CAR sequences that may be included within a modulating agent are any sequences specifically bound by an adhesion molecule. As used herein, an "adhesion molecule" is any molecule that mediates cell adhesion via a receptor on the cell's surface. Adhesion molecules include members of the cadherin gene superfamily that are not classical cadherins (e.g., proteins that do not contain an HAV sequence and/or one or more of the other characteristics recited above for classical cadherins), such as desmogleins (Dsg) and desmocollins (Dsc); integrins; and other uncategorized transmembrane proteins, such as occludin, as well as extracellular matrix proteins such as laminin, fibronectin, collagens, vitronectin, entactin and tenascin. Preferred CAR sequences for inclusion within a modulating agent include (a) Arg-Gly-Asp (RGD), which is bound by integrins (see Cardarelli et al., *J. Biol. Chem.* 267:23159–64, 1992); (b) the occludin CAR sequence LYHY (SEQ ID NO:35); (c) the CAR sequence for junctional adhesion molecule (JAM) SFTIDPKSG (SEQ ID NO:57) or DPK; (d) claudin CAR sequences comprising at least four consecutive amino acids present within a claudin region that has the formula: Trp-Lys/Arg-Aaa-Baa-Ser/Ala-Tyr/Phe-Caa-Gly (SEQ ID NO:36), wherein Aaa, Baa and Caa indicate independently selected amino acid residues; Lys/Arg is an amino acid that is lysine or arginine; Ser/Ala is an amino acid that is serine or alanine; and Tyr/Phe is an amino acid that is tyrosine or phenylalanine; and (e) non-classical cadherin CAR sequences comprising at least three consecutive amino acids present within a nonclassical cadherin region that has the formula: Aaa-Phe-Baa-Ile/Leu/Val- Asp/Asn/Glu-Caa-Daa-Ser/Thr/Asn-Gly (SEQ ID NO:37), wherein Aaa, Baa, Caa and Daa are independently selected amino acid residues; Ile/Leu/Val is an amino acid that is selected from the group consisting of isoleucine, leucine and valine, Asp/Asn/Glu is an amino acid that is selected from the group consisting of aspartate, asparagine and glutamate; and Ser/Thr/Asn is an amino acid that is selected from the group consisting of serine, threonine or asparagine. Representative claudin CAR sequences include IYSY (SEQ ID NO:38), TSSY (SEQ ID NO:39), VTAF (SEQ ID NO:40) and VSAF (SEQ ID NO:41). Representative nonclassical cadherin CAR sequences include the VE-cadherin (cadherin-5) CAR sequence DAE; the OB-cadherin (cadherin-11) CAR sequences DDK, EEY and EAQ; and the dsg CAR sequences NQK, NRN and NKD; the dsc CAR sequences EKD and ERD.

Linkers may, but need not, be used to separate CAR sequences and/or antibody sequences within a modulating agent. A linker may be any molecule (including peptide and/or non-peptide sequences as well as single amino acids or other molecules), that does not contain a CAR sequence and that can be covalently linked to at least two peptide sequences. Using a linker, HAV-containing cyclic peptides and other peptide or protein sequences may be joined head-to-tail (i.e., the linker may be covalently attached to the carboxyl or amino group of each peptide sequence), head-to-side chain and/or tail-to-side chain. Modulating agents comprising one or more linkers may form linear or branched structures. Within one embodiment, modulating agents having a branched structure comprise three different CAR sequences, such as RGD, YIGSR (SEQ ID NO:33) and HAV, one or more of which are present within a cyclic peptide. Within another embodiment, modulating agents having a branched structure comprise RGD, YIGSR (SEQ ID NO:33), HAV and KYSFNYDGSE (SEQ ID NO:34). In a third embodiment, modulating agents having a branched structure comprise HAV and LYHY (SEQ ID NO:35), along with one or more of NQK, NRN, NKD, EKD and ERD. Bi-functional modulating agents that comprise an HAV sequence with flanking E-cadherin-specific sequences joined via a linker to an HAV sequence with flanking N-cadherin-specific sequences are also preferred for certain embodiments.

Linkers preferably produce a distance between CAR sequences between 0.1 to 10,000 nm, more preferably about 0.1–400 nm. A separation distance between recognition sites may generally be determined according to the desired function of the modulating agent. In general, the linker distance should be small (0.1–400 nm). One linker that can be used for such purposes is $(H_2N(CH_2)_nCO_2H)_m$, or derivatives thereof where n ranges from 1 to 10 and m ranges from 1 to 4000. For example, if glycine ($H_2NCH_2CO_2H$) or a multimer thereof is used as a linker, each glycine unit corresponds to a linking distance of 2.45 angstroms, or 0.245 nm, as determined by calculation of its lowest energy conformation when linked to other amino acids using molecular modeling techniques. Similarly, aminopropanoic acid corresponds to a linking distance of 3.73 angstroms, aminobutanoic acid to 4.96 angstroms, aminopentanoic acid to 6.30 angstroms and amino hexanoic acid to 6.12 angstroms. Other linkers that may be used will be apparent to those of ordinary skill in the art and include, for example, linkers based on repeat units of 2,3-diaminopropanoic acid, lysine and/or ornithine. 2,3-Diaminopropanoic acid can provide a linking distance of either 2.51 or 3.11 angstroms depending on whether the side-chain amino or terminal amino is used in the linkage. Similarly, lysine can provide linking distances of either 2.44 or 6.95 angstroms and ornithine 2.44 or 5.61 angstroms. Peptide and non-peptide linkers may generally be incorporated into a modulating agent using any appropriate method known in the art.

Modulating agents may contain one HAV sequence or multiple HAV sequences, which may be adjacent to one another (ie., without intervening sequences) or in close proximity (i.e., separated by peptide and/or non-peptide linkers to give a distance between the CAR sequences that ranges from about 0.1 to 400 nm). Within one such embodiment, the cyclic peptide contains two HAV sequences. Such a modulating agent may additionally comprise a CAR sequence for one or more different adhesion molecules (including, but not limited to, other CAMs) and/or one or more antibodies or fragments thereof that bind to such sequences. Linkers may, but need not, be used to separate such CAR sequence(s) and/or antibody sequence(s) from the HAV sequence(s) and/or each other. Such modulating agents may generally be used within methods in which it is desirable to simultaneously disrupt cell adhesion mediated by multiple adhesion molecules. Within certain preferred embodiments, the second CAR sequence is derived from fibronectin and is recognized by an integrin (i.e., RGD; see Cardarelli et al., *J. Biol. Chem.* 267:23159–23164, 1992), or is an occludin CAR sequence (e.g., LYHY; SEQ ID NO:35). One or more antibodies, or fragments thereof, may similarly be used within such embodiments.

Modulating agents and cyclic peptides as described herein may comprise residues of L-amino acids, D-amino acids, or any combination thereof Amino acids may be from natural or non-natural sources, provided that at least one amino group and at least one carboxyl group are present in the molecule; α- and β-amino acids are generally preferred. The 20 L-amino acids commonly found in proteins are identified herein by the conventional three-letter or one-letter abbreviations indicated in Table 1, and the corresponding D-amino acids are designated by a lower case one letter symbol. Modulating agents and cyclic peptides may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having an N-acetyl group (such that the amino group that represents the N-terminus of the linear peptide prior to cyclization is acetylated) and/or a C-terminal amide group (i.e., the carboxy terminus of the linear peptide prior to cyclization is amidated). Residues other than common amino acids that may be present with a cyclic peptide include, but are not limited to, penicillamine, β,β-tetramethylene cysteine, β,β-pentamethylene cysteine, β-mercaptopropionic acid, β,β-pentamethylene-β-mercaptopropionic acid, 2-mercaptobenzene, 2-mercaptoaniline, 2-mercaptoproline, ornithine, diaminobutyric acid, α-aminoadipic acid, m-aminomethylbenzoic acid and α,β-diaminopropionic acid.

TABLE 1

Amino acid one-letter and three-letter abbreviations

| | | |
|---|---|---|
| A | Ala | Alanine |
| R | Arg | Arginine |
| D | Asp | Aspartic acid |
| N | Asn | Asparagine |
| C | Cys | Cysteine |
| Q | Gln | Glutamine |
| E | Glu | Glutamic acid |
| G | Gly | Glycine |
| H | His | Histidine |
| I | Ile | Isoleucine |
| L | Leu | Leucine |
| K | Lys | Lysine |
| M | Met | Methionine |
| F | Phe | Phenylalanine |
| P | Pro | Proline |
| S | Ser | Serine |
| T | Thr | Threonine |
| W | Trp | Tryptophan |
| Y | Tyr | Tyrosine |
| V | Val | Valine |

Modulating agents and cyclic peptides as described herein may be synthesized by methods well known in the art, including recombinant DNA methods and chemical synthesis. Chemical synthesis may generally be performed using standard solution phase or solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1–4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.* 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for α-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthoganol systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and p-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Acetylation of the N-terminal can be accomplished by reacting the final peptide with acetic anhydride before cleavage from the resin. C-amidation is accomplished using an appropriate resin such as methylbenzhydrylamine resin using the Boc technology.

Following synthesis of a linear peptide, with or without N-acetylation and/or C-amidation, cyclization may be achieved by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. This method suffers from the disadvantage of being slow but has the advantage of only producing $H_2O$ as a side product. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Cyclic peptides produced by this method require purification using standard techniques, but this oxidation is applicable at acid pHs. By way of example, strong oxidizing agents can be used to perform the cyclization shown below (SEQ ID NOs: 58 and 42), in which the underlined portion is cyclized:

FmocCysAsp(t-Bu)GlyTyr(t-Bu)ProLys(Boc)Asp(t-Bu)CysLys(t-Bu)Gly-OMe→Fmoc
<u>CysAsp(t-Bu)GlyTyr(t-Bu)ProLys(Boc)Asp(t-Bu)Cys</u> Lys(t-Bu)Gly-OMe Oxidizing agents also allow concurrent deprotection/oxidation of suitable S-protected linear precursors to avoid premature, nonspecific oxidation of free cysteine, as shown below (SEQ ID NOs: 43 and 44), where X and Y=S-Trt or S-Acm:

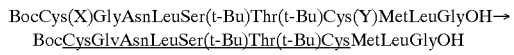

BocCys(X)GlyAsnLeuSer(t-Bu)Thr(t-Bu)Cys(Y)MetLeuGlyOH→
BocCysGlyAsnLeuSer(t-Bu)Thr(t-Bu)CysMetLeuGlyOH

DMSO, unlike $I_2$ and $K_3Fe(CN)_6$, is a mild oxidizing agent which does not cause oxidative side reactions of the nucleophilic amino acids mentioned above. DMSO is miscible with $H_2O$ at all concentrations, and oxidations can be performed at acidic to neutral pHs with harmless byproducts. Methyltrichlorosilane-diphenylsulfoxide may alternatively be used as an oxidizing agent for concurrent deprotection/oxidation of S-Acm, S-Tacm or S-t-Bu of cysteine without affecting other nucleophilic amino acids. There are no polymeric products resulting from intermolecular disulfide bond formation. In the example below (SEQ ID NOs: 45 and 46), X is Acm, Tacm or t-Bu:

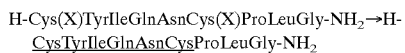

H-Cys(X)TyrIleGlnAsnCys(X)ProLeuGly-NH$_2$→H-
CysTyrIleGlnAsnCysProLeuGly-NH$_2$

Suitable thiol-containing residues for use in such oxidation methods include, but are not limited to, cysteine, β,β-dimethyl cysteine (penicillamine or Pen), β,β-tetramethylene cysteine (Tmc), β,β-pentamethylene cysteine (Pmc), β-mercaptopropionic acid (Mpr), β,β-pentamethylene-β-mercaptopropionic acid (Pmp), 2-mercaptobenzene, 2-mercaptoaniline and 2-mercaptoproline. Peptides containing such residues are illustrated by the following representative formulas, in which the underlined portion is cyclized, N-acetyl groups are indicated by N—Ac and C-terminal amide groups are represented by —NH$_2$:

i) N-Ac-<u>Cys-His-Ala-Val-Cys</u>-NH$_2$ (SEQ ID NO:10)
ii) N-Ac-<u>Cys-Ala-His-Ala-Val-Asp-Ile-Cys</u>-NH$_2$ (SEQ ID NO:18)
iii) N-Ac-<u>Cys-Ser-His-Ala-Val-Cys</u>-NH$_2$ (SEQ ID NO:24)
iv) N-Ac-<u>Cys-His-Ala-Val-Ser-Cys</u>-NH$_2$ (SEQ ID NO:25)
v) N-Ac-<u>Cys-Ala-His-Ala-Val-Asp-Cys</u>-NH$_2$ (SEQ ID NO:19)
vi) N-Ac-<u>Cys-Ser-His-Ala-Val-Ser-Ser-Cys</u>-NH$_2$ (SEQ ID NO:27)
vii) N-Ac-<u>Cys-His-Ala-Val-Ser-Cys</u>-OH (SEQ ID NO:25)
viii) H-<u>Cys-Ala-His-Ala-Val-Asp-Cys</u>-NH$_2$ (SEQ ID NO:19)
ix) N-Ac-<u>Cys-His-Ala-Val-Pen</u>-NH$_2$ (SEQ ID NO:47)
x) N-Ac-Ile-<u>Tmc-Tyr-Ser-His-Ala-Val-Ser-Cys</u>-Glu-NH$_2$ (SEQ ID NO:48)
xi) N-Ac-Ile-<u>Pmc-Tyr-Ser-His-Ala-Val-Ser-Ser-Cys</u>-NH$_2$ (SEQ ID NO:49)
xii) <u>Mpr-Tyr-Ser-His-Ala-Val-Ser-Ser-Cys</u>-NH$_2$ (SEQ ID NO:50)
xiii) <u>Pmp-Tyr-Ser-His-Ala-Val-Ser-Ser-Cys</u>-NH$_2$ (SEQ ID NO:51)

xii)
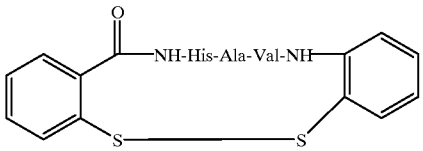

xiii)
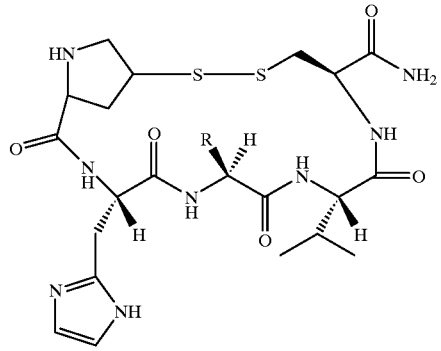

It will be readily apparent to those of ordinary skill in the art that, within each of these representative formulas, any of the above thiol-containing residues may be employed in place of one or both of the thiol-containing residues recited.

Within another embodiment, cyclization may be achieved by amide bond formation. For example, a peptide bond may be formed between terminal functional groups (i.e., the amino and carboxy termini of a linear peptide prior to cyclization). Two such cyclic peptides are AHAVDI (SEQ ID NO:23) and SHAVSS (SEQ ID NO:29), with or without an N-terminal acetyl group and/or a C-terminal amide. Within another such embodiment, the linear peptide comprises a D-amino acid (e.g., HAVsS; SEQ ID NO:52). Alternatively, cyclization may be accomplished by linking one terminus and a residue side chain or using two side chains, as in KHAVD (SEQ ID NO:12) or KSHAVSSD (SEQ ID NO:30), with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate.

Methods for forming amide bonds are well known in the art and are based on well established principles of chemical reactivity. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. The formation of the inactive N-acylurea, resulting from O→N migration, can be circumvented by converting the O-acylurea to an active ester by reaction with an N-hydroxy compound such as 1-hydroxybenzotriazole, 1-hydroxysuccinimide, 1-hydroxynorbornene carboxamide or ethyl 2-hydroximino-2-cyanoacetate. In addition to minimizing O→N migration, these additives also serve as catalysts during cyclization and assist in lowering racemization. Alternatively, cyclization can be performed using the azide method, in which a reactive azide intermediate is generated from an alkyl ester via a hydrazide. Hydrazinolysis of the terminal ester necessitates the use of a t-butyl group for the protection of side chain carboxyl functions in the acylating component. This limitation can be overcome by using diphenylphosphoryl acid (DPPA), which furnishes an azide directly upon reaction with a carboxyl group. The slow reactivity of azides and the formation of isocyanates by their disproportionation restrict the usefulness of this method. The mixed anhydride method of lactam formation is widely used because of the facile removal of reaction by-products. The anhydride is formed upon reaction of the carboxylate anion with an alkyl chloroformate or pivaloyl chloride. The attack of the amino component is then guided to the carbonyl carbon of the acylating component by the electron donating effect of the alkoxy group or by the steric bulk of the pivaloyl chloride t-butyl group, which obstructs attack on the wrong carbonyl group. Mixed anhydrides with phosphoric acid derivatives have also been successfully used. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. The last few years have witnessed the development of benzotriazolyloxytris-(dimethylamino) phosphonium hexafluorophosphonate (BOP) and its congeners as advantageous coupling reagents. Their performance is generally superior to that of the well established carbodiimide amide bond formation reactions.

Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF. Examples of thiol-containing linkages are shown below:

i.

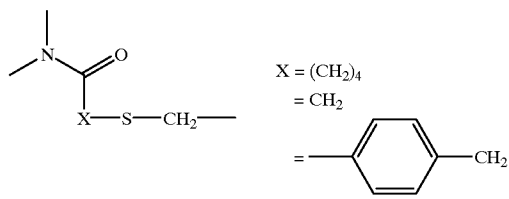

ii.

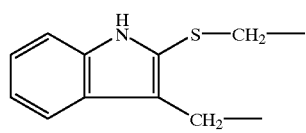

Cyclization may also be achieved using $\delta_1,\delta_1$-Ditryptophan (i.e., Ac-<u>Trp-Gly-Gly-Trp</u>-OMe) (SEQ ID NO:53), as shown below:

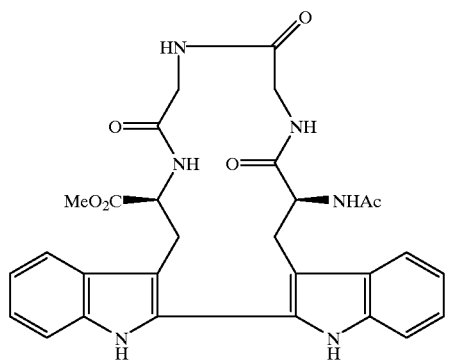

Representative structures of cyclic peptides are provided in FIG. 3. Within FIG. 3, certain cyclic peptides having the ability to modulate cell adhesion (shown on the left) are paired with similar inactive structures (on the right). The structures and formulas recited herein are provided solely for the purpose of illustration, and are not intended to limit the scope of the cyclic peptides described herein.

As noted above, a modulating agent may consist entirely of one or more cyclic peptides, or may contain additional peptide and/or non-peptide sequences, which may be linked to the cyclic peptide(s) using conventional techniques. Peptide portions may be synthesized as described above or may be prepared using recombinant methods. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of an endogenous cadherin or other adhesion molecule. Such sequences may be prepared based on known cDNA or genomic sequences (see Blaschuk et al., *J. Mol. Biol.* 211:679–682, 1990), or from sequences isolated by screening an appropriate library with probes designed based on the sequences of known cadherins. Such screens may generally be performed as described in Sambrook et al., *Molecular Cloning: A Laboratory Manual*, Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous adhesion molecule. To generate a nucleic acid molecule encoding a peptide portion of a modulating agent, an endogenous sequence may be modified using well known techniques. For example, portions encoding one or more CAR sequences may be joined, with or without separation by nucleic acid regions encoding linkers, as discussed above. Alternatively, portions of the desired nucleic acid sequences may be synthesized using well known techniques, and then ligated together to form a sequence encoding a portion of the modulating agent.

As noted above, portions of a modulating agent may comprise an antibody, or antigen-binding fragment thereof, that specifically binds to a CAR sequence. As used herein, an antibody, or antigen-binding fragment thereof, is said to "specifically bind" to a CAR sequence (with or without flanking amino acids) if it reacts at a detectable level (within, for example, an ELISA, as described by Newton et al., *Develop. Dynamics* 197:1–13, 1993) with a peptide containing that sequence, and does not react detectably with peptides containing a different CAR sequence or a sequence in which the order of amino acid residues in the cadherin CAR sequence and/or flanking sequence is altered.

Antibodies and fragments thereof may be prepared using standard techniques. See, e.g., Harlow and Lane, *Antibodies: A Laboratory Manual*, Cold Spring Harbor Laboratory, 1988. In one such technique, an immunogen comprising a CAR sequence is initially injected into any of a wide variety of mammals (e.g., mice, rats, rabbits, sheep or goats). Small immunogens (i.e., less than about 20 amino acids) should be joined to a carrier protein, such as bovine serum albumin or keyhole limpet hemocyanin. Following one or more injections, the animals are bled periodically. Polyclonal antibodies specific for the CAR sequence may then be purified from such antisera by, for example, affinity chromatography using the modulating agent or antigenic portion thereof coupled to a suitable solid support.

Monoclonal antibodies specific for a CAR sequence may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the modulating agent or antigenic portion thereof. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation, and extraction. Antibodies having the desired activity may generally be identified using immunofluorescence analyses of tissue sections, cell or other samples where the target cadherin is localized.

Within certain embodiments, monoclonal antibodies may be specific for particular cadherins (e.g., the antibodies bind to E-cadherin, but do not bind significantly to N-cadherin, or vise versa). Such antibodies may be prepared as described above, using an immunogen that comprises (in addition to the HAV sequence) sufficient flanking sequence to generate the desired specificity (e.g., 5 amino acids on each side is generally sufficient). One representative immunogen is the 15-mer FHLRAHAVDINGNQV-NH$_2$ (SEQ ID NO:54), linked to KLH (see Newton et al., *Dev. Dynamics* 197:1–13, 1993). To evaluate the specificity of a particular antibody, representative assays as described herein and/or conventional antigen-binding assays may be employed. Such antibodies may generally be used for therapeutic, diagnostic and assay purposes, as described herein. For example, such antibodies may be linked to a drug and administered to a mammal to target the drug to a particular cadherin-expressing cell, such as a leukemic cell in the blood.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988; see especially page 309) and digested by papain to yield Fab and Fc fragments. The Fab and Fc fragments may be separated by affinity chromatography on protein A bead columns (Harlow and Lane, 1988, pages 628–29).

Evaluation of Modulating Agent Activity

As noted above, cyclic peptides and other modulating agents as described herein are capable of modulating classical cadherin-mediated cell adhesion, particularly N-cadherin-mediated adhesion. The ability of a modulating agent to modulate cell adhesion may generally be evaluated in vitro by assaying the effect of the cyclic peptide on adhesion of one or more cells that express a classical cadherin, such as cancer cells.

An initial screen for the ability to modulate classical cadherin-mediated cell adhesion may be performed by evaluating the ability of a modulating agent to bind to a classical cadherin using any binding assay known to those of ordinary skill in the art. For example, a Pharmacia Biosensor machine may be used, as discussed in Jonsson et al., *Biotechniques* 11:520–27, 1991. A specific example of a technology that measures the interaction of peptides with molecules can be found in Williams et al., *J. Biol. Chem.* 272, 22349–22354, 1997. Alternatively, real-time BIA (Biomolecular Interaction Analysis) uses the optical phenomenon surface plasmon resonance to monitor biomolecular interactions. The detection depends upon changes in the mass concentration of macromolecules at the biospecific interface, which in turn depends upon the immobilization of test molecule or peptide (referred to as the ligand) to the surface of a Biosensor chip, followed by binding of the interacting molecule (referred to as the analyte) to the ligand. Binding to the chip is measured in real-time in arbitrary units of resonance (RU).

By way of example, surface plasmon resonance experiments may be carried out using a BIAcore X™ Biosensor (Pharmacia Ltd., BIAcore, Uppsala, Sweden). Parallel flow cells of CM 5 sensor chips may be derivatized, using the amine coupling method, with streptavidin (200 μg/ml) in 10 mM Sodium Acetate, pH 4.0, according to the manufacturer's protocol. Approximately 2100–2600 resonance units (RU) of ligand may be immobilized, corresponding to a concentration of about 2.1–2.6 ng/mm$^2$. The chips may then coated be with a classical cadherin (or portion thereof) derivatized to biotin. Any non-specifically bound protein is removed.

To determine binding, test analytes (e.g., peptides containing the CAR sequence) may be placed in running buffer and passed simultaneously over test and control flow cells. After a period of free buffer flow, any analyte remaining bound to the surface may be removed with, for example, a pulse of 0.1% SDS bringing the signal back to baseline. Specific binding to the derivatized sensor chips may be determined automatically by the system by subtraction of test from control flow cell responses. In general, a modulating agent binds to a classical cadherin at a detectable level within such as assay. The level of binding is preferably at least that observed for the full length classical cadherin under similar conditions.

To confirm modulation of cell adhesion, cells that express a classical cadherin may be used. A "cadherin-expressing cell," as used herein, may be any type of cell that expresses at least one cadherin on the cell surface at a detectable level, using standard techniques such as immunocytochemical protocols (Blaschuk and Farookhi, *Dev. Biol.* 136:564–567, 1989). Cadherin-expressing cells include endothelial (e.g., bovine pulmonary artery endothelial cells), epithelial and/or cancer cells (e.g., the human ovarian cancer cell line SKOV3 (ATCC #HTB-77)). For example, such cells may be plated under standard conditions that permit cell adhesion in the presence and absence of modulating agent (e.g., 500 µg/mL). Disruption of cell adhesion may be determined visually within 24 hours, by observing retraction of the cells from one another. In general, a modulating agent is an inhibitor of cell adhesion if, within such an assay, contact of the test cells with 500 µg/mL of the modulating agent results in a discernible disruption of cell adhesion. For use within the methods provided herein, a modulating agent should disrupt adhesion of at least one type of cancer cell.

Modulating Agent Modification and Formulations

A modulating agent as described herein may, but need not, be linked to one or more additional molecules. For example, although modulating agents as described herein may preferentially bind to specific tissues or cells, and thus may be sufficient to target a desired site in vivo, it may be beneficial for certain applications to include an additional targeting agent. Accordingly, a targeting agent may also, or alternatively, be linked to a modulating agent to facilitate targeting to one or more specific tissues. As used herein, a "targeting agent," may be any substance (such as a compound or cell) that, when linked to a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. Among the many monoclonal antibodies that may serve as targeting agents are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. An antibody targeting agent may be an intact (whole) molecule, a fragment thereof, or a functional equivalent thereof. Examples of antibody fragments are F(ab')2, -Fab', Fab and F[v] fragments, which may be produced by conventional methods or by genetic or protein engineering. Linkage is generally covalent and may be achieved by, for example, direct condensation or other reactions, or by way of bi- or multifunctional linkers. Within other embodiments, it may also be possible to target a polynucleotide encoding a modulating agent to a target tissue, thereby increasing the local concentration of modulating agent. Such targeting may be achieved using well known techniques, including retroviral and adenoviral infection.

For certain embodiments, it may be beneficial to also, or alternatively, link a drug to a modulating agent. As used herein, the term "drug" refers to any bioactive agent intended for administration to a mammal to prevent or treat a disease or other undesirable condition. Drugs include hormones, growth factors, proteins, peptides and other compounds.

Within certain aspects of the present invention, one or more modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. A modulating agent (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration. For certain topical applications, formulation as a cream or lotion, using well known components, is preferred.

For certain embodiments, as discussed below, a pharmaceutical composition may further comprise a modulator of cell adhesion that is mediated by one or more molecules other than cadherins. Such modulators may generally be prepared as described above, incorporating one or more non-cadherin CAR sequences and/or antibodies thereto in place of the cadherin CAR sequences and antibodies. Such compositions are particularly useful for situations in which it is desirable to inhibit cell adhesion mediated by multiple cell-adhesion molecules, such as other members of the cadherin gene superfamily that are not classical cadherins (e.g., Dsg and Dsc); claudins; integrins; members of the immunoglobulin supergene family, such as N-CAM; and other uncategorized transmembrane proteins, such as occludin, as well as extracellular matrix proteins such as laminin, fibronectin, collagens, vitronectin, entactin and tenascin. Preferred CAR sequences for use are as described above.

A pharmaceutical composition may also contain one or more drugs, which may be linked to a modulating agent or may be free within the composition. Virtually any drug may be administered in combination with a modulating agent as described herein for a variety of purposes as described below. Examples of types of drugs that may be administered with a modulating agents include analgesics, anesthetics, antianginals, antifungals, antibiotics, anticancer drugs (e.g., taxol or mitomycin C), antiinflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antiphsychotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary antiinfectives. Preferred drugs are anticancer agents, or other drugs suitable for use in a cancer patient.

The compositions described herein may be administered as part of a sustained release formulation (i.e., a formulation such as a capsule or sponge that effects a slow release of modulating agent following administration). Such formulations may generally be prepared using well known technology and administered by, for example, oral, rectal or subcutaneous implantation, or by implantation at the desired target site. Sustained-release formulations may contain a cyclic peptide dispersed in a carrier matrix and/or contained within a reservoir surrounded by a rate controlling membrane (see, e.g., European Patent Application 710,491 A). Carriers for use within such formulations are biocompatible, and may also be biodegradable; preferably the formulation provides a relatively constant level of cyclic peptide release. The amount of modulating agent contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented). Appropriate dosages and the duration and frequency of administration will be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably 0.0001% to 0.2%, and more preferably from 0.0001% to 0.002%. Fluid compositions typically contain about 10 ng/ml to 5 mg/ml, preferably from about 10 $\mu$g to 2 mg/mL modulating agent. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Modulating Agent Methods of Use

In general, the modulating agents and compositions described herein may be used for modulating the adhesion of cadherin-expressing cells (i.e., cells that express one or more of E-cadherin, N-cadherin, P-cadherin, R-cadherin and/or other cadherin(s) containing the HAV sequence, including as yet undiscovered cadherins) in vitro and/or in vivo. As noted above, modulating agents may comprise a cyclic peptide containing a single HAV sequence, multiple HAV sequences in close proximity and/or an antibody (or an antigen-binding fragment thereof) that recognizes a cadherin CAR sequence. When it is desirable to also disrupt cell adhesion mediated by other adhesion molecules, a modulating agent may additionally comprise one or more CAR sequences bound by such adhesion molecules (and/or antibodies or fragments thereof that bind such sequences), preferably separated from each other and from the HAV sequence by linkers. As noted above, such linkers may or may not comprise one or more amino acids. Within the methods described herein, one or more modulating agents may generally be administered alone, or within a pharmaceutical composition. In each specific method described herein, as noted above, a targeting agent may be employed to increase the local concentration of modulating agent at the target site.

The present invention provides methods for inhibiting the development of a cancer (i.e., for treating or preventing cancer and/or inhibiting metastasis) in a mammal. Cancers that may be treated using modulating agents provided herein include, but are not limited to, carcinomas, melanomas and leukemias. Preferably, a modulating agent prevents detectable tumor growth and results in a substantial decrease in tumor size (i.e., a reduction of at least 50%).

A modulating agent may be administered alone or within a pharmaceutical composition. For melanomas and certain other accessible tumors, injection or topical administration as described above may be preferred. For ovarian cancers, administration may be achieved by flushing the peritoneal cavity with a composition comprising one or more modulating agents. Other tumors (e.g., bladder tumors, bronchial tumors or tracheal tumors) may be treated by injection of a modulating agent into the cavity. In other instances, the composition may be administered systemically, and targeted to the tumor using any of a variety of specific targeting agents, as described above. In general, the amount of modulating agent administered varies depending upon the method of administration and the nature of the cancer, but may vary within the ranges identified above. The effectiveness of the cancer treatment or inhibition of metastasis may be evaluated using well known clinical observations such as the level of serum markers (e.g., CEA or PSA).

The following Examples are offered by way of illustration and not by way of limitation.

EXAMPLE 1

Preparation of Representative Cyclic Peptides

This Example illustrates the solid phase synthesis of representative cyclic peptides.

The peptides were assembled on methylbenzhydrylamine resin (MBHA resin) for the C-terminal amide peptides. The traditional Merrifield resins were used for any C-terminal acid peptides. Bags of a polypropylene mesh material were filled with the resin and soaked in dichloromethane. The resin packets were washed three times with 5% diisopropylethylamine in dichloromethane and then washed with dichloromethane. The packets are then sorted and placed into a Nalgene bottle containing a solution of the amino acid of interest in dichloromethane. An equal amount of diisopropylcarbodiimide (DIC) in dichloromethane was added to activate the coupling reaction. The bottle was shaken for one hour to ensure completion of the reaction. The reaction mixture was discarded and the packets washed with DMF. The N-$\alpha$-Boc was removed by acidolysis using a 55% TFA in dichloromethane for 30 minutes leaving the TFA salt of the $\alpha$-amino group. The bags were washed and the synthesis completed by repeating the same procedure while substituting for the corresponding amino acid at the coupling step. Acetylation of the N-terminal was performed by reacting the peptide resins with a solution of acetic anhydride in dichloromethane in the presence of diisopropylethylamine. The peptide was then side-chain deprotected and cleaved from the resin at 0° C. with liquid HF in the presence of anisole as a carbocation scavenger.

The crude peptides were purified by reversed-phase high-performance liquid chromatography. Purified linear precursors of the cyclic peptides were solubilized in 75% acetic acid at a concentration of 2–10 mg/mL. A 10% solution of iodine in methanol was added dropwise until a persistent coloration was obtained. A 5% ascorbic acid solution in water was then added to the mixture until discoloration. The disulfide bridge containing compounds were then purified by HPLC and characterized by analytical HPLC and by mass spectral analysis.

EXAMPLE 2

Disruption of Human Ovarian Cancer Cell Adhesion

This Example illustrates the use of a representative cyclic peptide to disrupt adhesion of human ovarian cancer cells.

The human ovarian cancer cell line SKOV3 (ATCC #HTB-77) expresses N-cadherin. SKOV3 cells were cultured in a modified MEM-based media containing 10% FCS. Cells were grown in T-250 culture flasks and maintained by periodic subculturing. Cyclic peptides were tested on cells grown in individual wells of 96-well culture dishes (surface area of each well was 0.32 cm$^2$). Cells were harvested from flasks and seeded at a density of 50,000 cells per well in 0.1 mL media containing the cyclic peptides at concentrations of 1, 0.1, or 0.01 mg/mL, or in the absence of cyclic peptide. Media control wells were also established. Cultures were evaluated periodically by microscopic examination under both bright field and phase contrast conditions. Cultures were maintained for 48 hours.

Figure 4A:
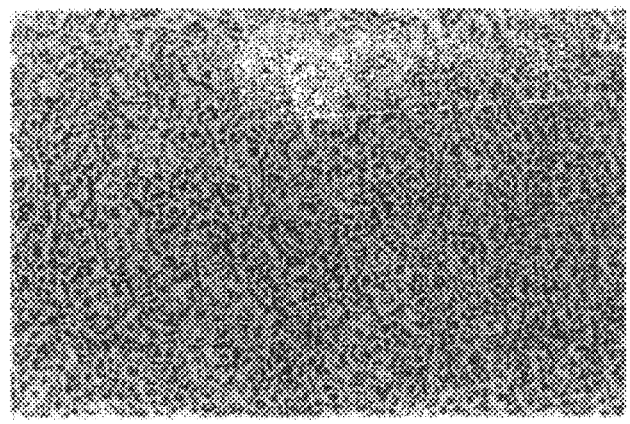
FIGS. 4A–4F are photographs showing monolayer cultures of human ovarian cancer cells (SKOV3) in the presence (FIGS. 4A and D–F) and absence (FIG. 4C) of a representative cyclic peptide or in the presence of an inactive control peptide (FIG. 4B).
Figure 4B:
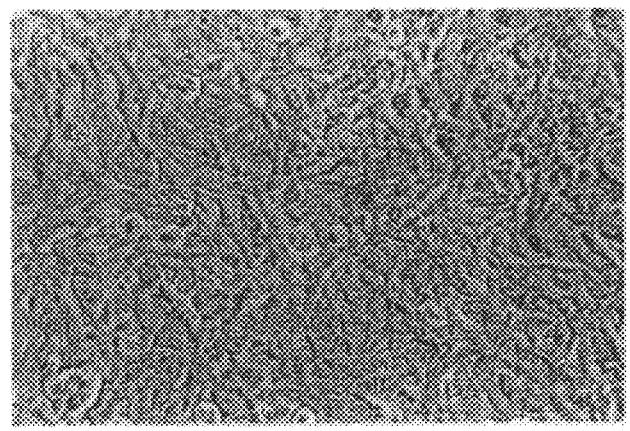
Figure 4C:
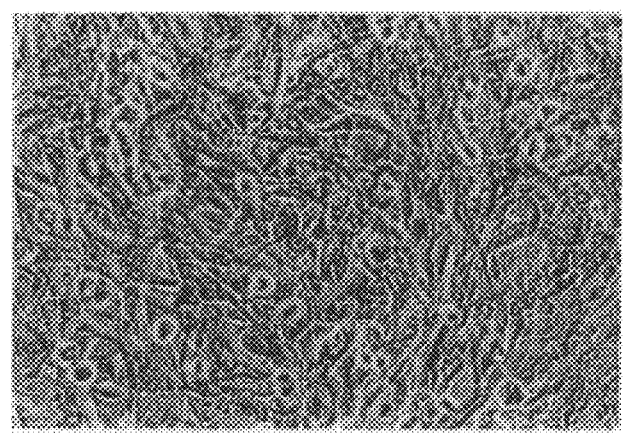
Figure 4D:
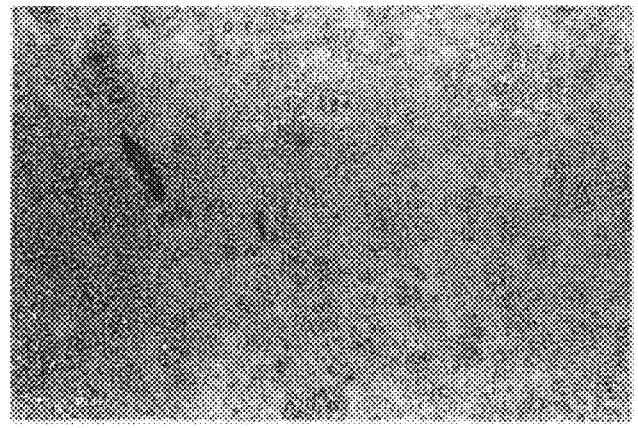
Figure 4E:
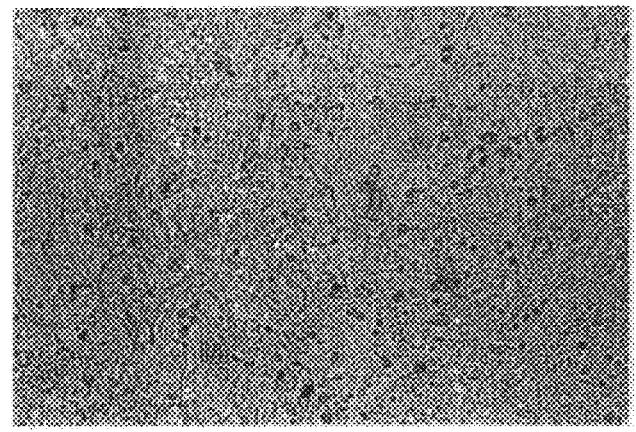
Figure 4F:
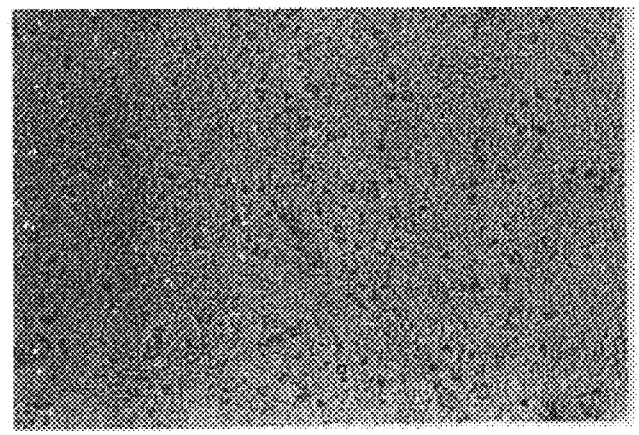
Figure 5A:
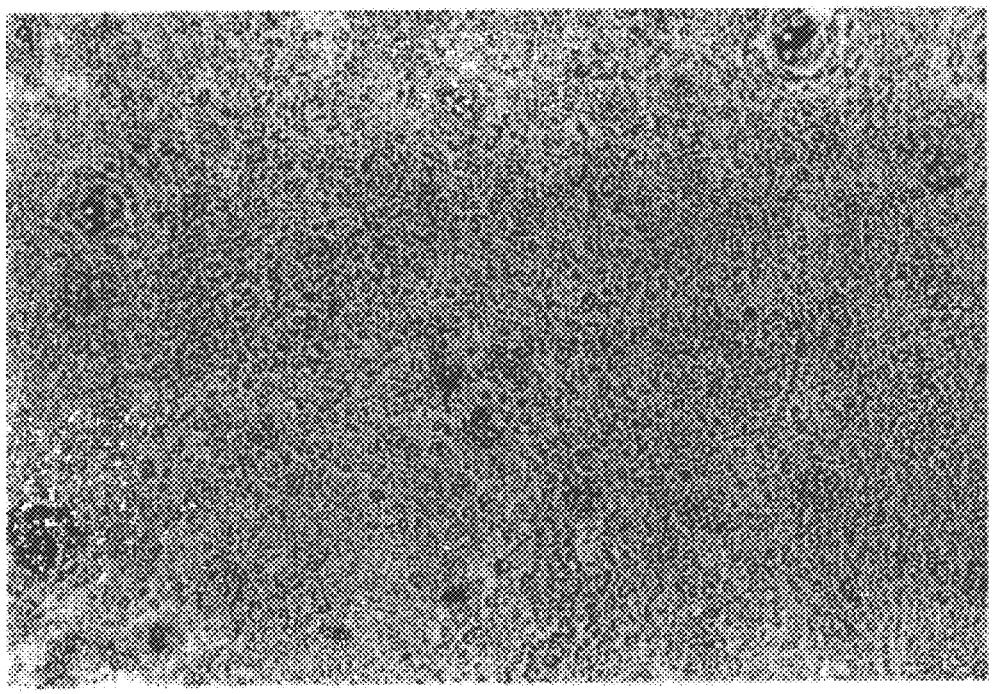
FIGS. 5A and 5B are photographs showing monolayer cultures of human ovarian cancer cells (SKOV3) 24 hours after exposure to 500 µg/mL of the representative cyclic peptide N-Ac-CHAVC-NH$_2$ (SEQ ID NO:10) (FIG. 5A) or the control peptide N-Ac-CHGVC-NH$_2$ (FIG. 5B; SEQ ID NO:11). Note that the SKOV3 cells round-up when cultured in the presence of 0.5 mg/ml N-Ac-CHAVC-NH$_2$ (SEQ ID NO:10).
Figure 5B:
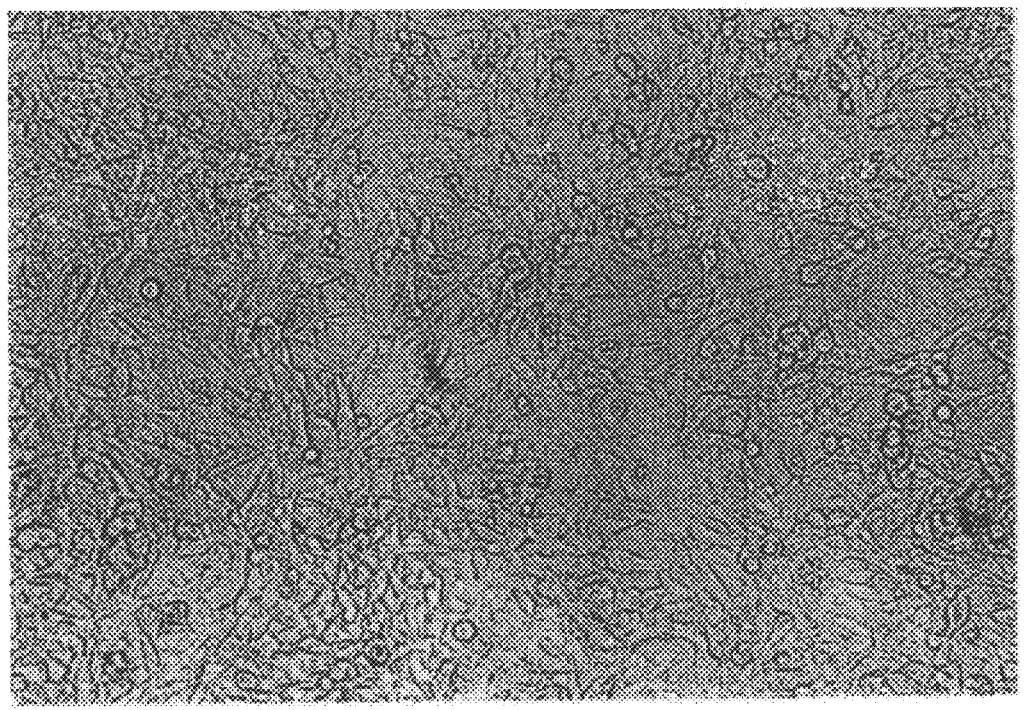

As shown in FIGS. 4A (compare to FIG. 4C) and 5A, the peptide N-Ac-CHAVC-NH$_2$ (final concentration of 1 mg/mL media; SEQ ID NO:10) disrupted SKOV3 cell adhesion within 24 hours, whereas the control N-Ac-CHGVC-NH$_2$ (SEQ ID NO:11) had no affect on cell adhesion (FIGS. 4B and 5B). The effect of different amounts of N-Ac-CHAVC-NH$_2$ (SEQ ID NO:10) after 48 hours is shown in FIGS. 4D–F. In the presence of N-Ac-CHGVC-NH$_2$, (FIGS. 4B and 5B; SEQ ID NO:11) the SKOV3 cells formed tightly adherent monolayers. In contrast, the SKOV3 cells did not spread onto the substrata, nor did they form tightly adherent monolayers in the presence of N-Ac-CHAVC-NH$_2$ (FIGS. 4A, 4D and 5A; SEQ ID NO:10). These data demonstrate that N-Ac-CHAVC-NH$_2$ (SEQ ID NO:10) is capable of inhibiting the function of human N-cadherin.

The cyclic peptides N-Ac-CAHAVDIC-NH$_2$ (SEQ ID NO:18), N-Ac-CAHAVDC-NH$_2$ (SEQ ID NO:19) and N-Ac-KHAVD-NH$_2$ (SEQ ID NO:12) were inactive in the SKOV3 cells, indicating that not all cyclic HAV-containing peptides are capable of disrupting cancer cell adhesion at concentrations of 0.01–1 mg/mL. It is not unexpected that the potencies of the cyclic peptides will vary.

EXAMPLE 3

Disruption of Human Ovarian Cancer Cell Adhesion

This Example further illustrates the ability of representative cyclic peptides to disrupt human ovarian cancer cell adhesion.

Figure 6A:
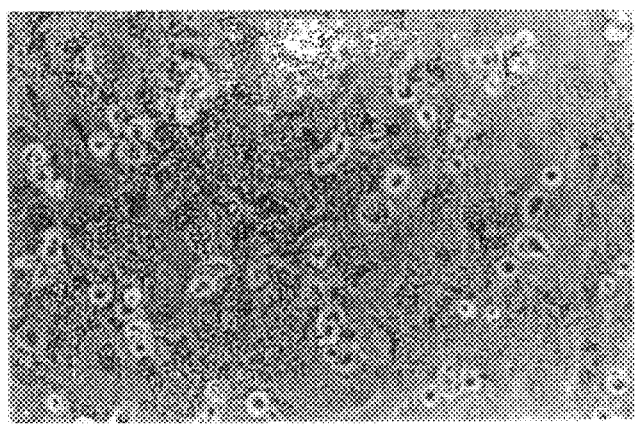
FIGS. 6A–6C are photographs showing monolayer cultures of human ovarian cancer cells (OVCAR3) in the presence of varying concentrations of a representative cyclic peptide.
Figure 6B:
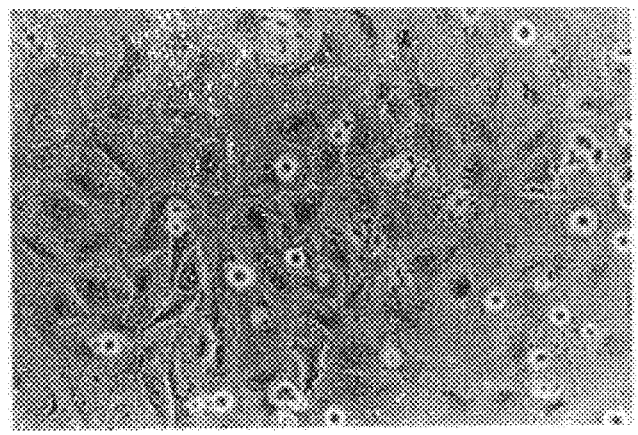
Figure 6C:
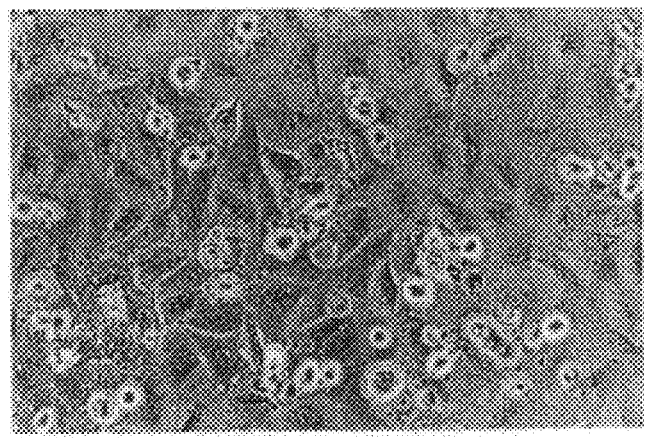

The human ovarian cancer cell line OVCAR-3, which expresses E-cadherin, was used in these experiments. Cells were cultured in RPMI supplemented with insulin and containing 20% FCS. Cells were grown in T-250 culture flasks and maintained by periodic subculturing. Cells were harvested from flasks and seeded in individual wells of 96-well culture dishes (surface area of each well was 0.32 cm$^2$) at a density of 50,000 cells per well in 0.1 ml media containing the cyclic peptides (at concentrations of 1, 0.1, or 0.01 mg/ml). Media control wells were also established. Cultures were evaluated periodically by microscopic examination under both bright field and phase contrast conditions, and were maintained for 48 hours. N-Ac-CHAVC-NH$_2$ (SEQ ID NO:10) was found to be inactive within this assay at these concentrations. However, the cyclic peptide N-Ac-CHAVSC-NH$_2$ (SEQ ID NO:25) disrupted OVCAR-3 adhesion (FIGS. 6A–C)). This data demonstrates that N-Ac-CHAVSC-NH$_2$ (SEQ ID NO:25) specifically affects cells that express E-cadherin.

EXAMPLE 4

Disruption of Melanoma Cell Adhesion

This Example illustrates the ability of a representative cyclic peptide to disrupt melanoma cell adhesion.

Melanoma ME115 cells (kindly provided by Meenhard Herlyn, Wistar Institute, Philadelphia, Pa.), which express N-cadherin were plated on glass coverslips and cultured for 24 hours in 50% keratinocyte growth medium (Clonetics, San Diego, Calif.) and 50% L15. Fresh medium containing the cyclic peptides (final concentration 500 μg/mL media) N-Ac-CHAVC-NH$_2$ (SEQ ID NO:10) or N-Ac-CHGVC-NH$_2$ (SEQ ID NO:11) was then added. Following 24 hours of culture in the presence of the peptides, the medium was removed and fresh medium containing the peptides was added. The cells were fixed 24 hours later with cold methanol and stored in phosphate buffered saline (PBS).

Coverslips were blocked for 1 hour in 3% ovalbumin/PBS and incubated for a further 1 hour in the presence of rabbit pan-cadherin antibody (Sigma Chemical Co., St. Louis, Mo.) diluted 1:500. Primary and secondary antibodies were diluted in PBS containing 6% normal goat serum. Following incubation in the primary antibody, coverslips were washed 3 times for 5 minutes each in PBS and incubated for 1 hour in goat anti-rabbit immunoglobulin G conjugated to fluorescein (Kiekegard and Perry, South San Francisco, Calif.) diluted 1:100. Following a further wash in PBS (3×5 minutes) coverslips were mounted in Vectashield (Vector Labs, Burlingame, Calif.) and viewed with a Zeiss infinity corrected microscope.

Figure 7A:
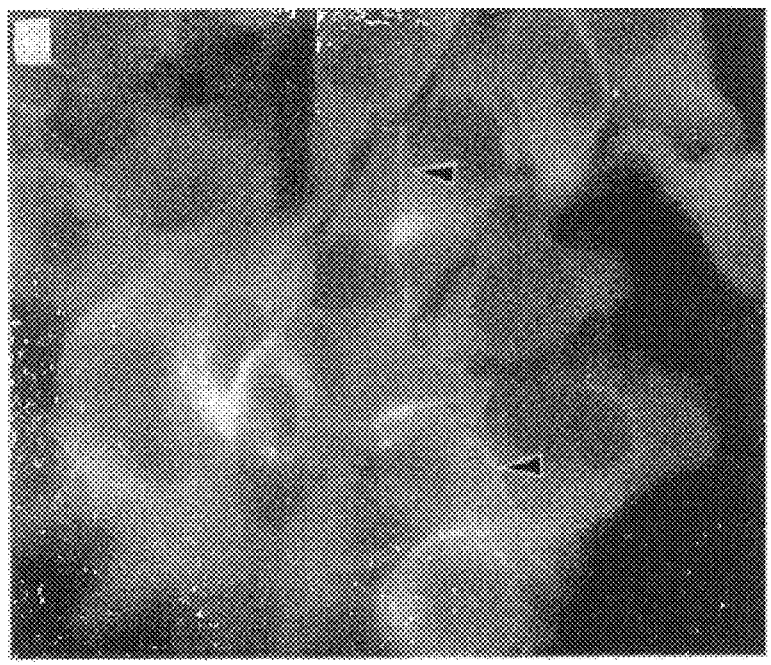
FIGS. 7A and 7B are photographs showing cultures of human melanoma ME115 cells in the presence (FIG. 7B) and absence (FIG. 7A) of a representative cyclic peptide. The cells were immunolabeled for N-cadherin.
Figure 7B:
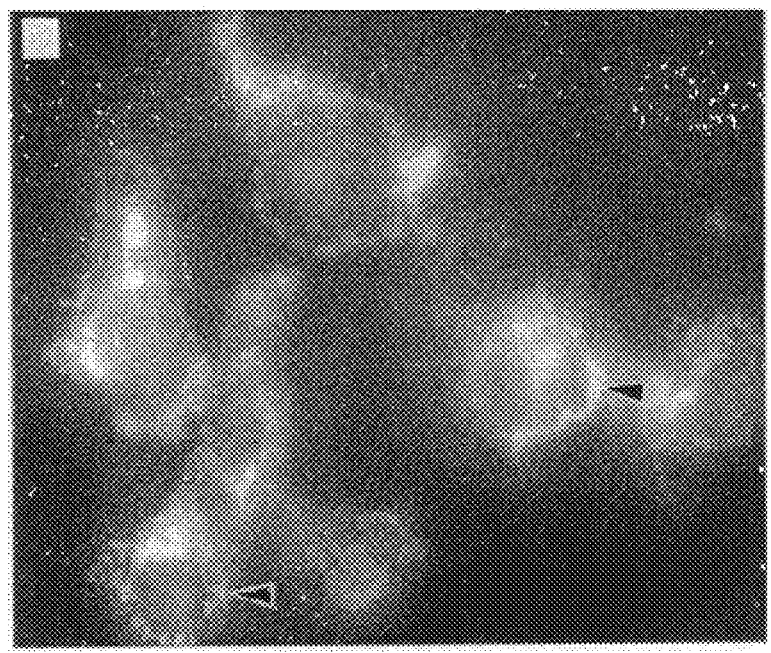

Photographs, shown in FIG. 7, show an absence of cell membrane staining and the appearance of bright intracellular vesicular staining in cells treated with N-Ac-CHAVC-NH$_2$ (SEQ ID NO:10). In contrast, cells exposed to N-Ac-CHGVC-NH$_2$ (SEQ ID NO:11) displayed cadherin staining all over the cell membrane. Occasionally, the staining concentrated at points of cell-cell contact. These results indicate that the representative cyclic peptide N-Ac-CHAVC-NH$_2$ (SEQ ID NO:10) disrupts melanoma cell adhesion.

EXAMPLE 5

Disruption of Breast Cancer Cell Adhesion

This Example illustrates the ability of a representative cyclic peptide to disrupt human breast epithelial cell adhesion.

A1N4 human breast epithelial cells (kindly provided by Martha Stampfer, Lawrence Berkeley Laboratory, Berkeley, Calif.) which express E-cadherin were plated on glass coverslips and cultured in F12/DME containing 0.5% FCS and 10 ng/mL EGF for 24 hours. Fresh medium containing the cyclic peptides (final concentration 500 μg/mL media) N-Ac-CHAVC-NH$_2$ (SEQ ID NO:10) or N-Ac-CHGVC-NH$_2$ (SEQ ID NO:11) was then added. Following 24 hours of culture in the presence of the peptides, the medium was removed and fresh medium containing the peptides was added. The cells were fixed 24 hours later with cold methanol and stored in phosphate buffered saline (PBS).

Coverslips were blocked for 1 hour in 3% ovalbumin/PBS and incubated for a further 1 hour in the presence of 1 μg/mL mouse anti-E-cadherin antibody (Zymed, Gaithersburg, Md.). Primary and secondary antibodies were diluted in PBS containing 6% normal goat serum. Following incubation in the primary antibody, coverslips were washed 3 times for 5 minutes each in PBS and incubated for 1 hour with goat anti-mouse conjugated to fluorescein (Kiekegard and Perry, South San Francisco, Calif.) diluted 1:100. Following a further wash in PBS (3×5 minutes) coverslips were mounted in Vectashield (Vector Labs, Burlingame, Calif.) and viewed with a Zeiss infinity corrected microscope.

Figure 8A:
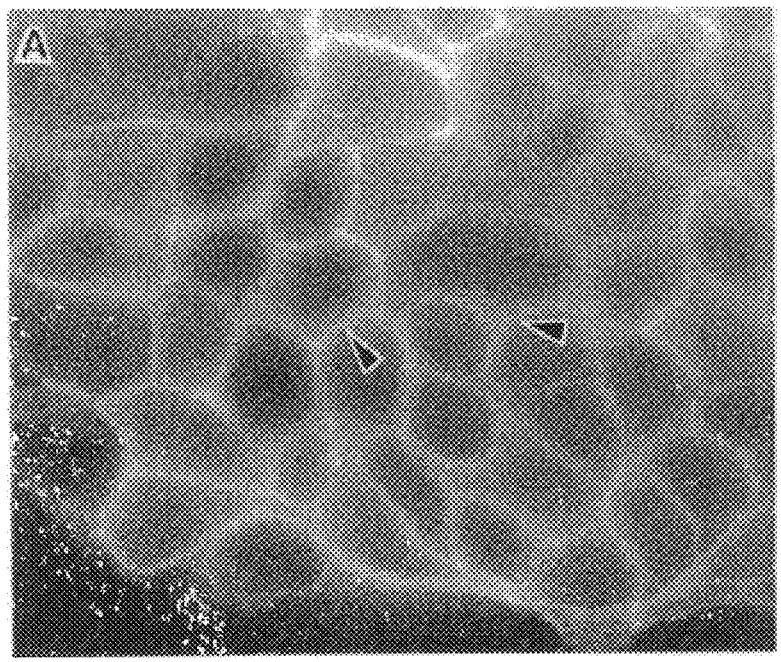
FIGS. 8A and 8B are photographs showing monolayer cultures of A1N4 human breast epithelial cells in the presence (FIG. 8B) and absence (FIG. 8A) of a representative cyclic peptide. The cells have been immunolabeled for E-cadherin.
Figure 8B:
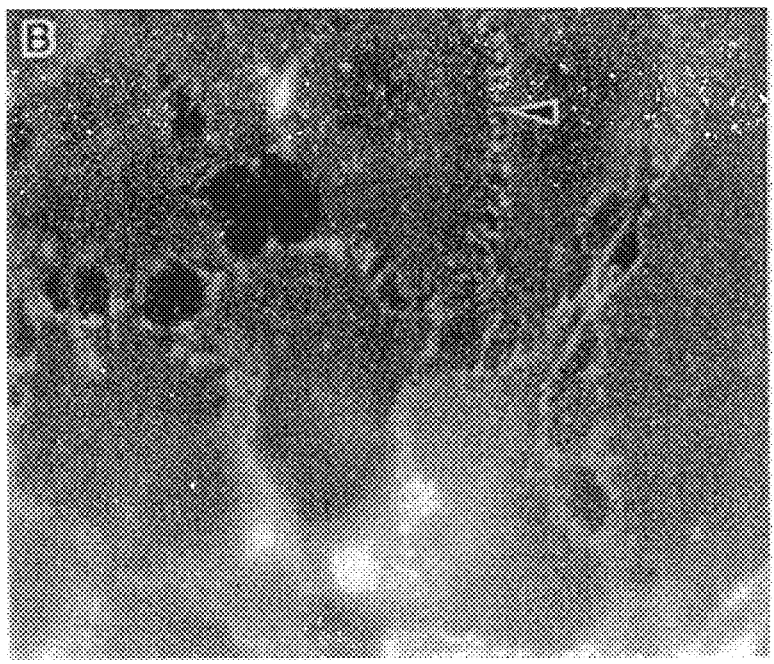
Figure 9:
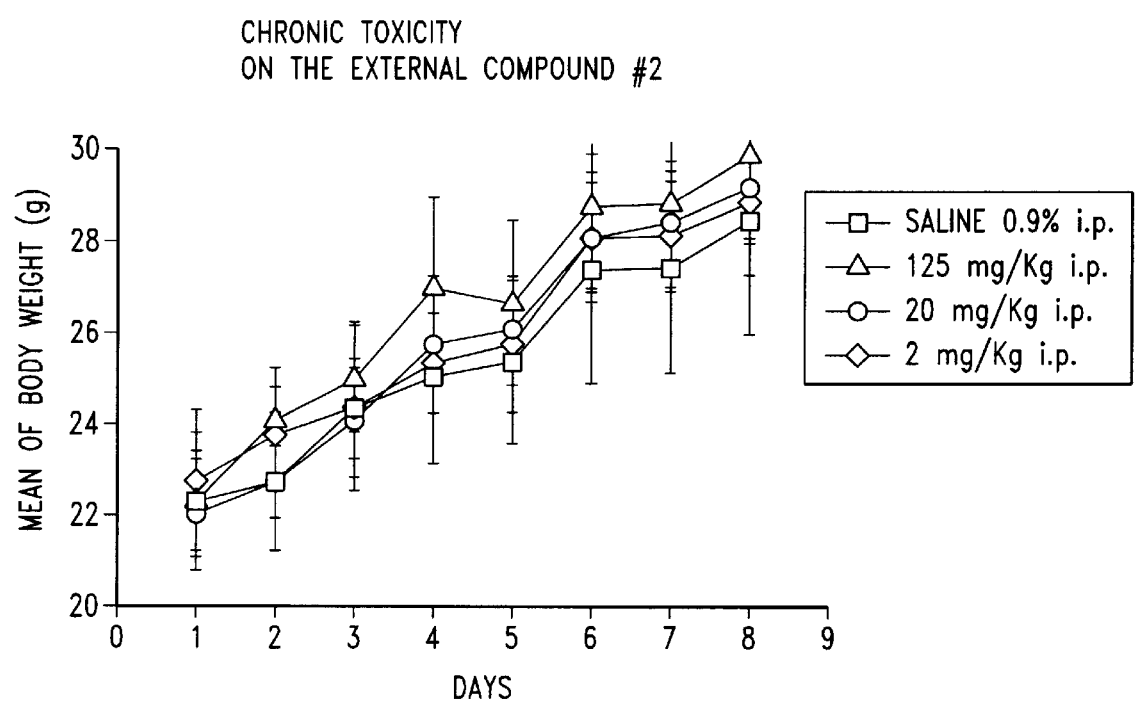
FIG. 9 is a graph illustrating the results of a study to assess the chronic toxicity of a representative cyclic peptide. The graph presents the mean body weight during the three-day treatment period (one intraperitoneal injection per day) and the four subsequent recovery days. Three different doses are illustrated, as indicated.

Photographs, shown in FIGS. 8A and 8B, show reduced E-cadherin staining with a stitched appearance in cells treated with N-Ac-CHAVC-NH$_2$ (SEQ ID NO:10). In addition, holes are present in the monolayer where the cells have retracted from one another. In contrast, cells exposed to N-Ac-CHGVC-NH$_2$ (SEQ ID NO:11) displayed E-cadherin staining concentrated at points of cell-cell contact and formed a tightly adherent monolayer.

EXAMPLE 6

Chronic Toxicity Study

This Example illustrates a toxicity study performed using a representative cyclic peptide.

Varying amounts of H-CHAVC-NH$_2$ (SEQ ID NO:10; 2 mg/kg, 20 mg/kg and 125 mg/kg) were injected into mice intraperitoneally every day for three days. During the recovery period (days 4–8), animals were observed for clinical symptoms. Body weight was measured (Table 22) and no significant differences occurred. In addition, no clinical symptoms were observed on the treatment or recovery days. Following the four day recovery period, autopsies were performed and no abnormalities were observed.

EXAMPLE 7

Stability of Cyclic Peptide in Blood

This Example illustrates the stability of a representative cyclic peptide in mouse whole blood.

Figure 10:
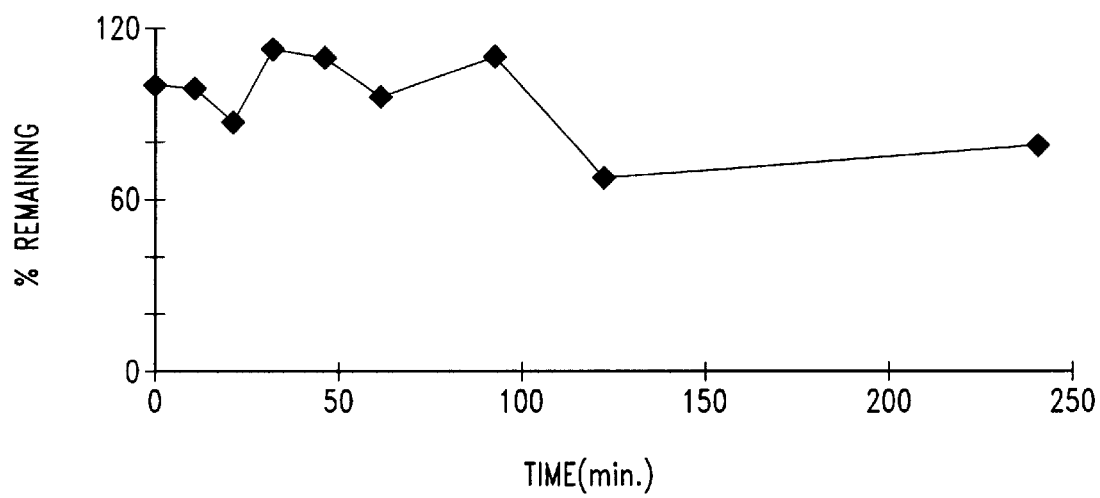
FIG. 10 is a graph illustrating the stability of a representative cyclic peptide in mouse whole blood. The percent of the cyclic peptide remaining in the blood was assayed at various time points, as indicated.

50 µl of a stock solution containing 12.5 µg/ml H-CHAVC-NH$_2$ (SEQ ID NO:10) was added to mouse whole blood and incubated at 37° C. Aliquots were removed at intervals up to 240 minutes, precipitated with acetonitrile, centrifuged and analyzed by HPLC. The results (Table 2 and FIG. 10) are expressed as % remaining at the various time points, and show generally good stability in blood.

TABLE 2

Stability of Representative Cyclic Peptide in Mouse Whole Blood

| Time (Min.) | Area 1 | Area 2 | Average | % Remaining |
| --- | --- | --- | --- | --- |
| 0 | 341344 | 246905 | 294124.5 | 100.00 |
| 10 | 308924 | 273072 | 290998 | 98.94 |
| 20 | 289861 | 220056 | 254958.5 | 86.68 |
| 30 | 353019 | 310559 | 331789 | 112.81 |
| 45 | 376231 | 270860 | 323545.5 | 110.00 |
| 60 | 373695 | 188255 | 280975 | 95.53 |
| 90 | 435555 | 216709 | 326132 | 110.88 |
| 120 | 231694 | 168880 | 200287 | 68.10 |
| 240 | 221952 | 242148 | 232050 | 78.90 |

EXAMPLE 8

Modulating Agent-Induced Reduction in Tumor Volume

This Example illustrates the use of a modulating agent for in vivo tumor reduction.

SKOV3 cells (ATCC) were grown to 70% confluence in Minimum Essential Medium (Life Technologies, Grand Island, N.Y.) supplemented with 10% Fetal Bovine Serum (Wisent, St. Bruno, Quebec) in a humidified atmosphere containing 5% CO$_2$. Cells were then dissociated with 0.02% PBS/EDTA. Total cell count and viable cell number was determined by trypan blue stain and a hemacytometer.

Approximately 1×10$^7$ cells were resuspended in 400 µl saline and injected in 6-week-old CD-1 nude mice (female, Charles River) subcutaneously. After 20 days of continuous tumor growth, tumor size was about 4.0 mm. The tumor-bearing animals were then injected intraperitoneally every day for 4 consecutive days with 20 mg/kg of the representative peptide modulating agent N-Ac-CHAVC-NH$_2$ (SEQ ID NO:10) and saline, for experimental and control respectively. Mice were sacrificed by cervical dislocation 4 days after final injection.

Figure 11A:
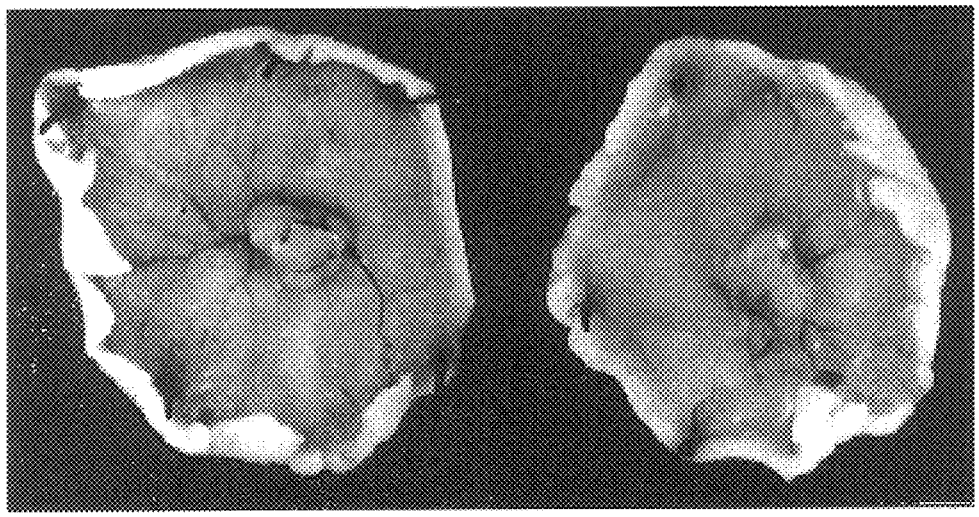
FIGS. 11A and 11B are photographs of human ovarian tumors grown in nude mice. Human ovarian cancer cells (SKOV3) were injected subcutaneously into nude mice. Tumors were grown to a size of 4 mm. Animals were then injected intraperitoneally, on four consecutive days, with 20 mg/kg of the representative cyclic peptide N-Ac-CHAVC-NH$_2$ (FIG. 11B; SEQ ID NO:10) or saline (FIG. 11A). Mice were sacrificed, and tumor tissue was sectioned and stained with hematoxylin/eosin.
Figure 11B:
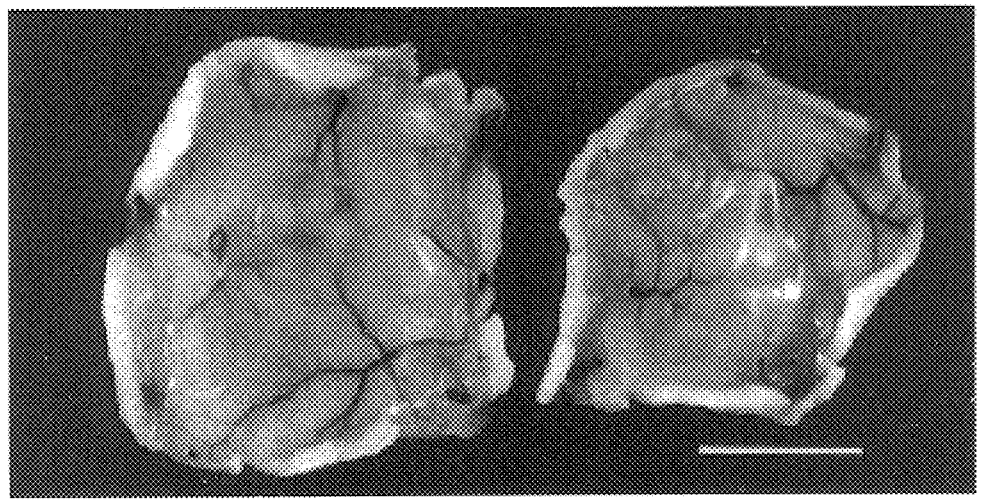

Tumor tissue was dissected and fixed in PBS with 4% paraformaldehyde for 48 hours. Specimens were then dehydrated in a series of alcohol incubations, and embedded in paraffin wax. Tissues were sectioned, rehydrated and stained with hematoxylin/eosin for morphological purposes. Representative sections obtained from treated and untreated mice are shown in FIGS. 11B and 11A, respectively.

Figure 12:
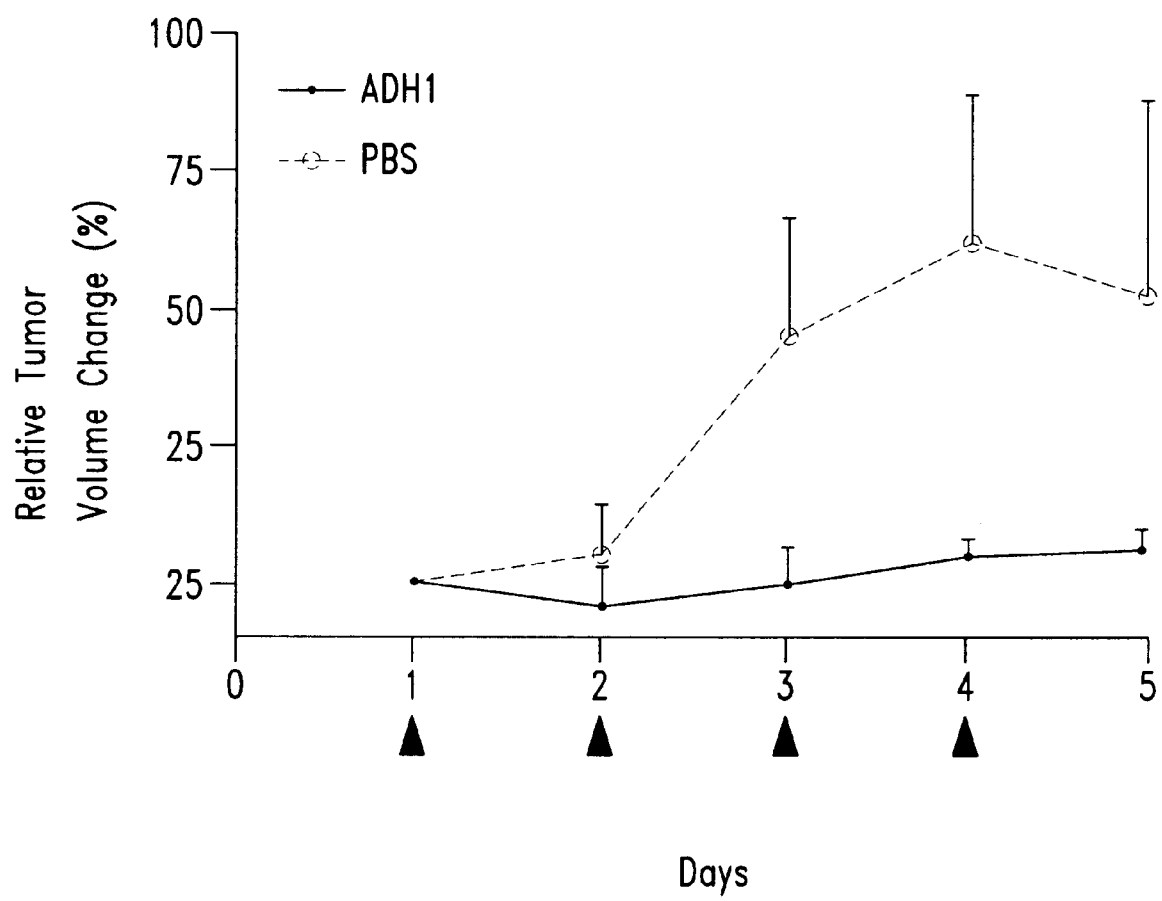
FIG. 12 is a graph showing the relative tumor volume change for human ovarian tumors in nude mice following intraperitoneal injection for four consecutive days as indicated, with 20 mg/kg of the representative cyclic peptide N-Ac-CHAVC-NH$_2$ (solid squares; SEQ ID NO:10) or saline (open squares).

FIG. 12 presents the results in graph form, showing the percent reduction in tumor volume over the four day treatment period. These data indicate that treatment with the cyclic peptide modulating agent prevents detectable tumor growth and results in a substantial decrease in tumor size, in comparison to the control.

Figures 13A, 13B:
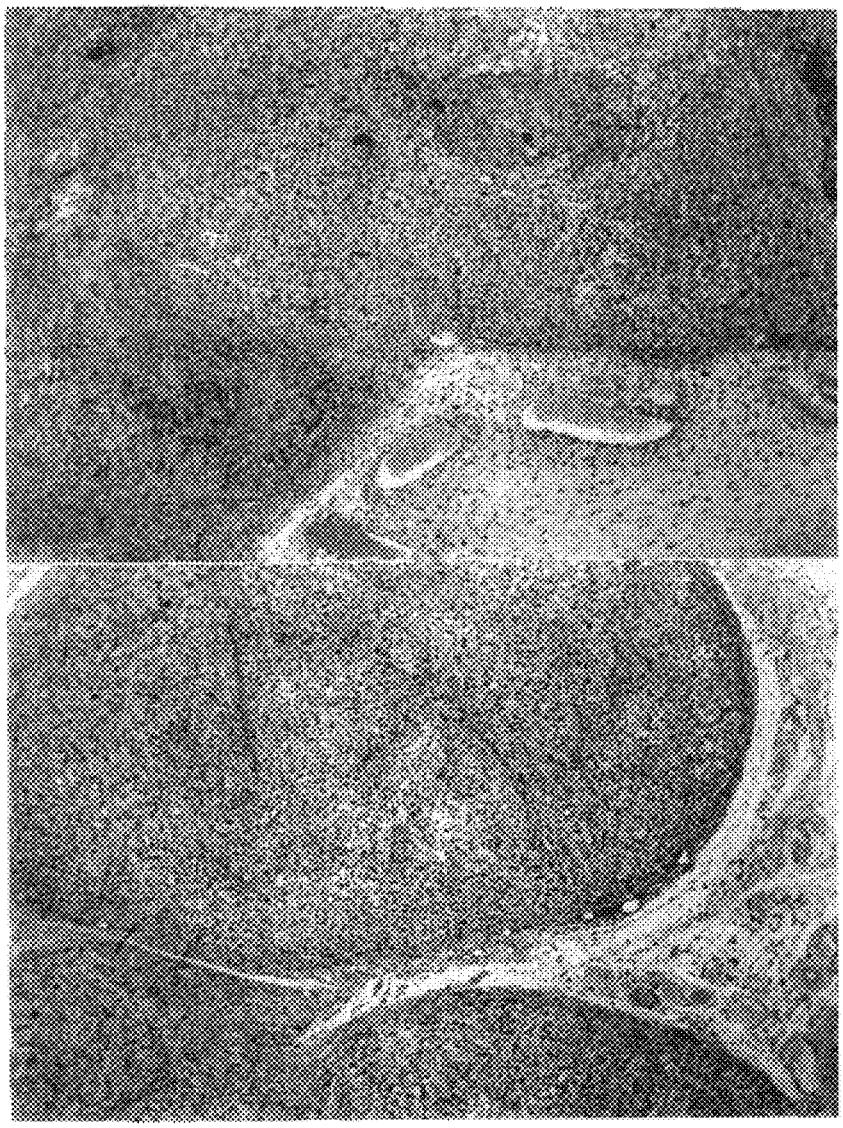
FIGS. 13A and 13B are photographs of human ovarian tumors grown in nude mice. Animals were injected intraperitoneally, on four consecutive days, with 2 mg/kg of the representative cyclic peptide modulating agent N-Ac-CHAVC-NH$_2$ (FIG. 13A; SEQ ID NO:10) or saline (FIG. 13B). Mice were sacrificed 24 hours after the last injection, and tumor tissue was sectioned and stained with hematoxylin/eosin.

Within similar experiments, tumor-bearing nude mice as described above were injected intraperitoneally with 2 mg/kg of the representative peptide modulating agent N-Ac-CHAVC-NH$_2$ (SEQ ID NO:10) and saline, for experimental and control respectively. Injections were performed every day for 4 days. Mice were sacrificed 24 hours after the last injection. Tumor tissue was fixed, sectioned and stained as described above. Representative sections obtained from treated and untreated mice are shown in FIGS. 13A and 13B, respectively.

Figure 14:
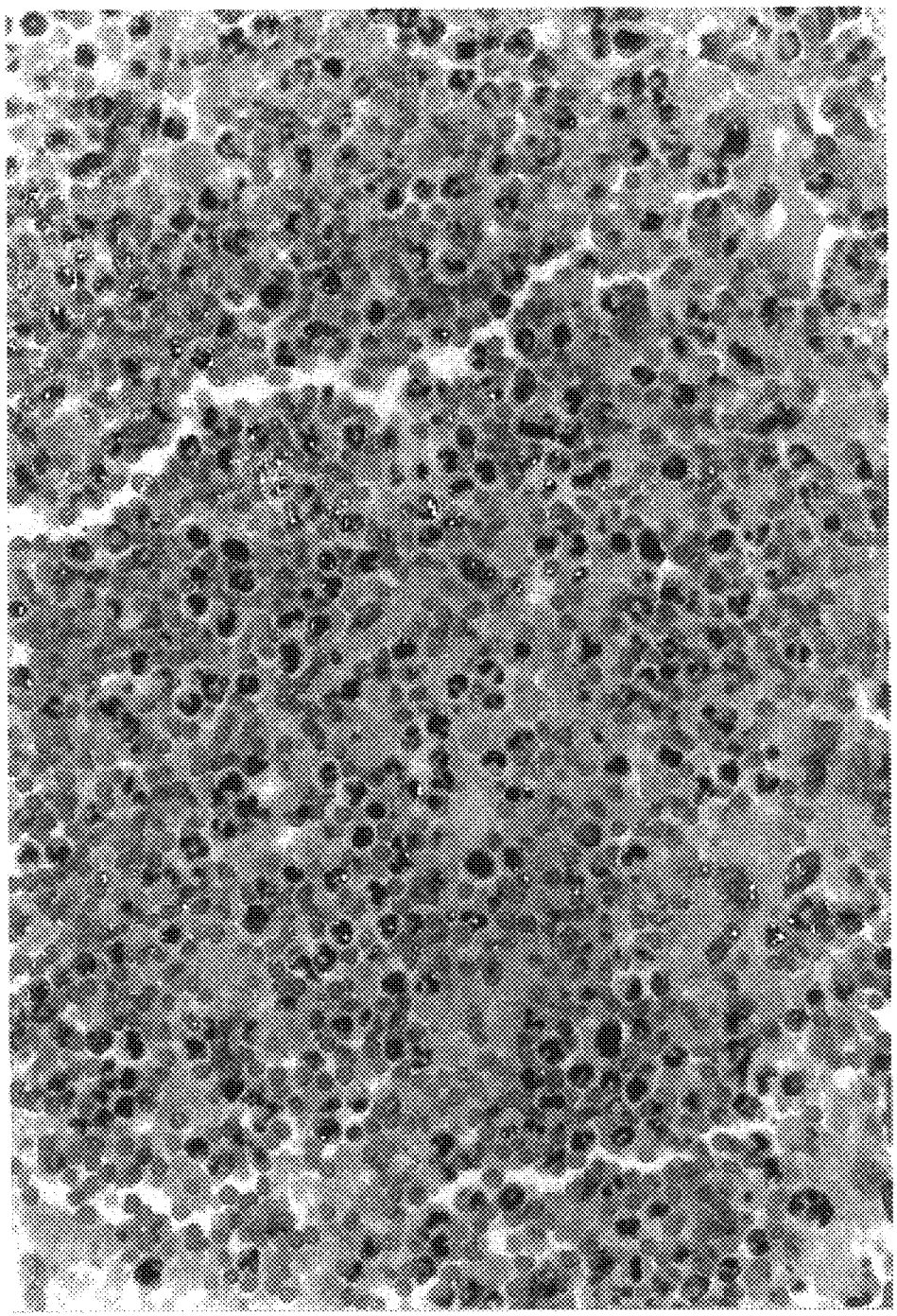
FIG. 14 is a photograph of a human ovarian tumor grown in a nude mouse, as described for FIG. 13A, showing leakage of red blood cells into the tumor mass.
Figure 15:
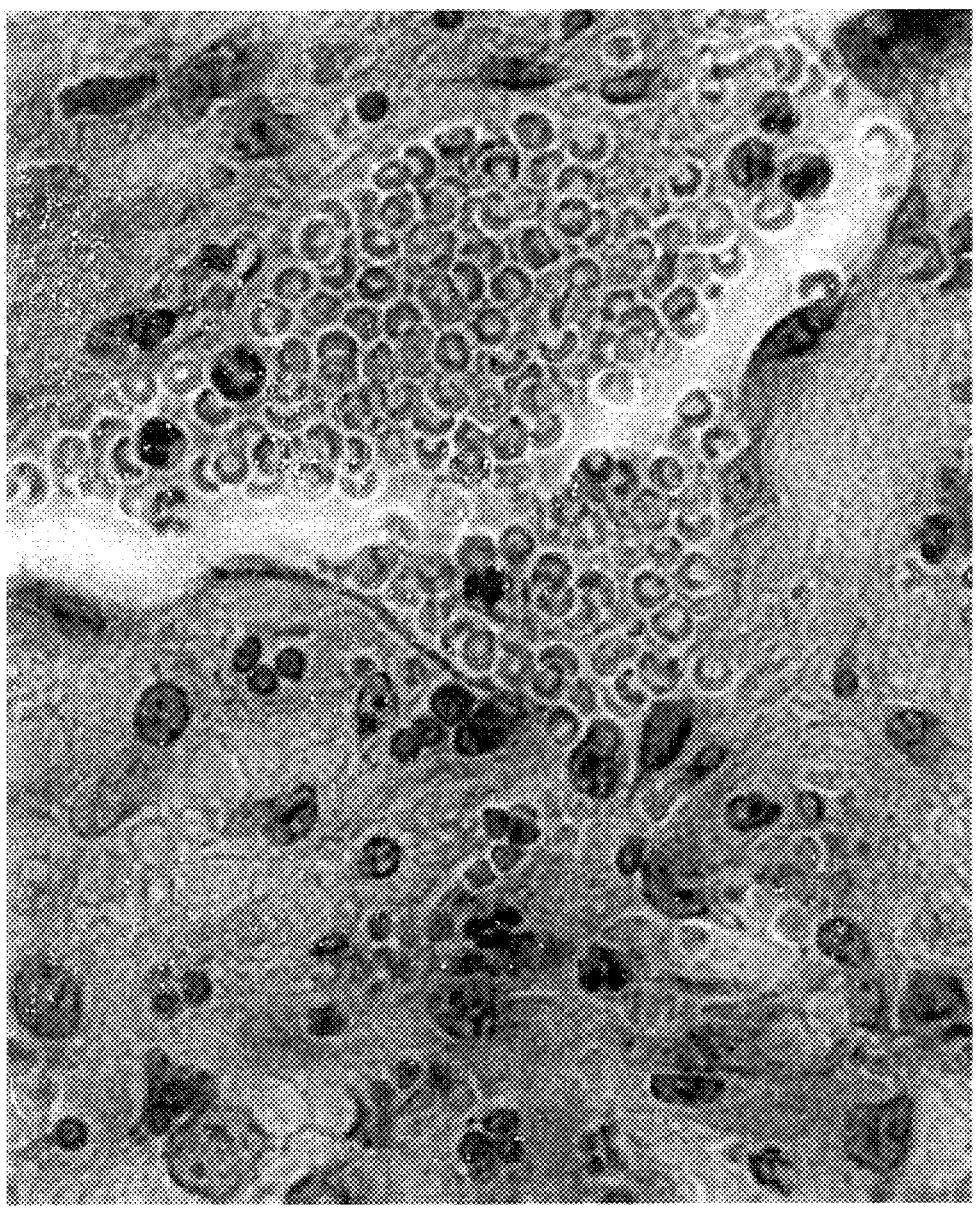
FIG. 15 is a photograph of a human ovarian tumor grown in a nude mouse, as described for FIG. 13A, showing a blood vessel that has been breached.

FIGS. 14 and 15 show close up images of the effect of the modulating agent on tumor blood vessels. In FIG. 14, red blood cells can be seen leaking into the tumor mass. FIG. 15 shows a blood vessel that has been breached and blood cells gathering and escaping at that point.

Figure 16:
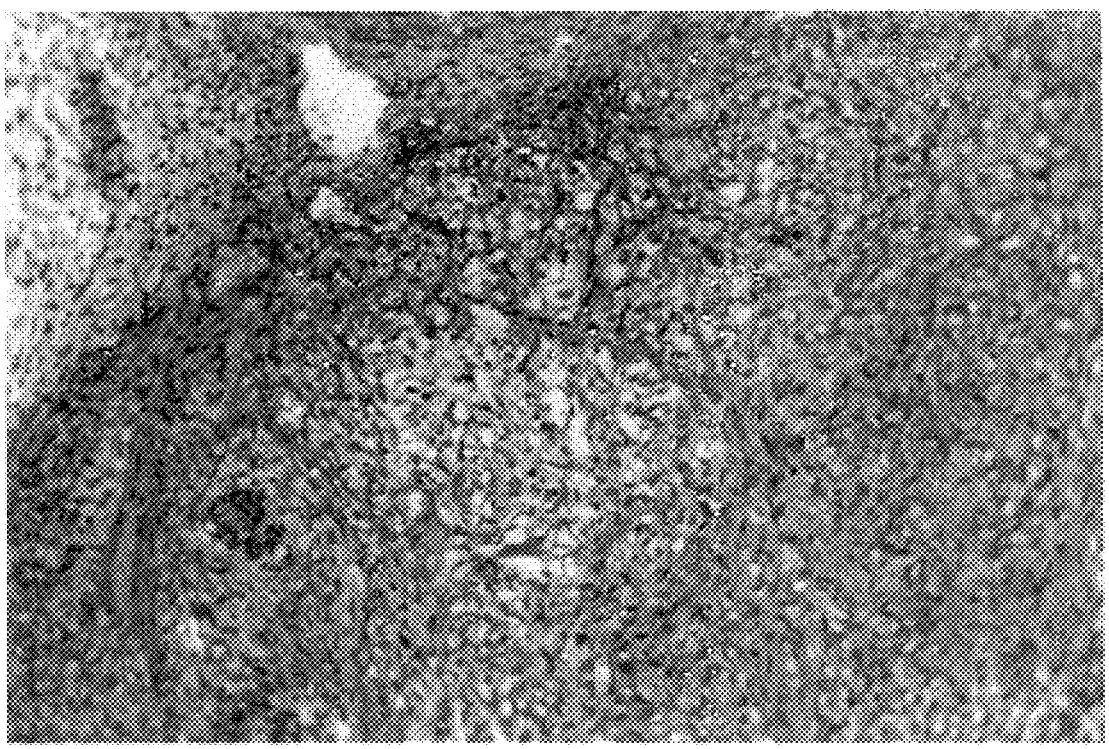
FIG. 16 is a photograph of a human ovarian tumor grown in a nude mouse, as described for FIG. 13B (i.e., untreated tumor), where the tumor section is stained for Von Willebrand Factor VIII.
Figure 17:
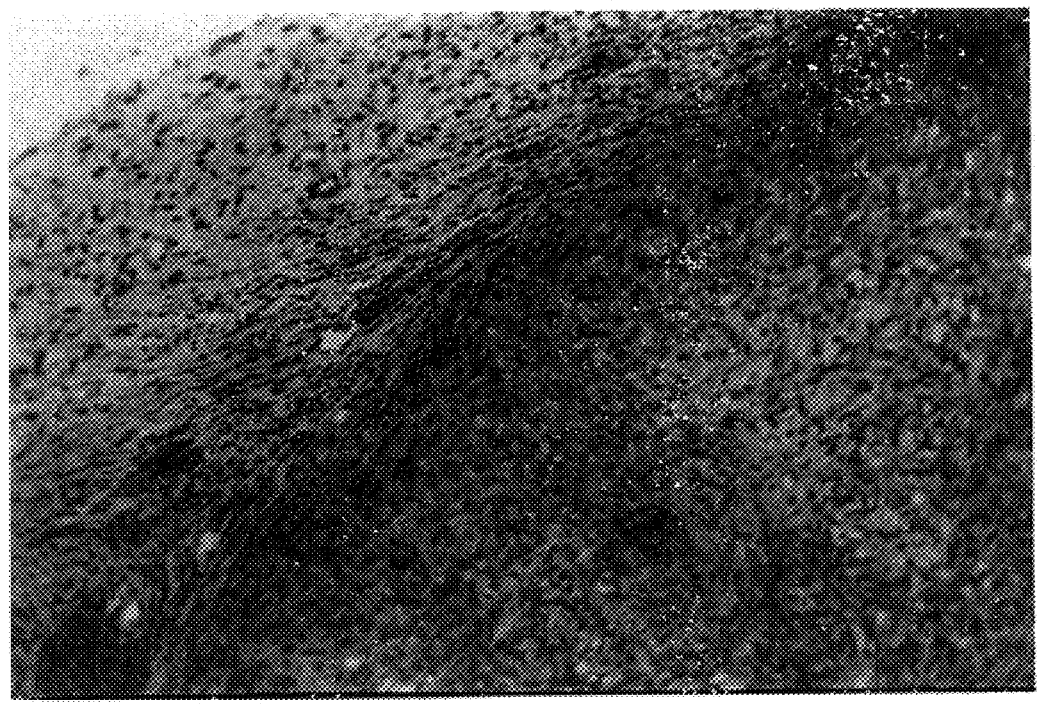
FIG. 17 is a photograph of a human ovarian tumor grown in a nude mouse, as described for FIG. 13A (i.e., tumor treated with the representative cyclic peptide modulating agent N-Ac-CHAVC-NH$_2$ (SEQ ID NO:10)), where the tumor section is stained for Von Willebrand Factor VIII.
Figure 18A:
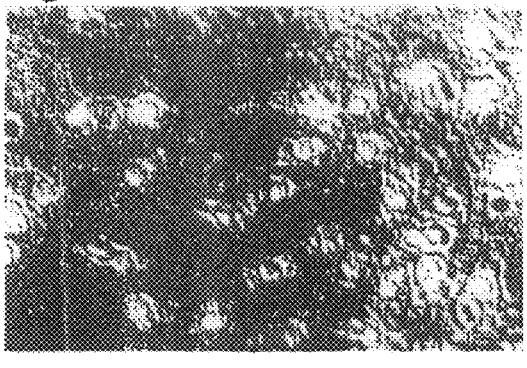
FIGS. 18A–18D are photographs illustrating the ability of a representative cyclic peptide to induce apoptosis in cancer cells. SKOV3 human ovarian cancer cells containing either N-Ac-CHAVC-NH$_2$ (SEQ ID NO:10) or a control peptide (N-Ac-CHGVC-NH$_2$; SEQ ID NO:1 1) in MEM with 10% FBS were plated onto poly-L-lysine coated glass slides. The cells were cultured for 48 hours and fixed with 4% paraformaldehyde for 30 minutes at room temperature. The slides were then washed three times with PBS and assessed for cell death using the In situ cell death detection kit (Boehringer Mannheim; Laval, Quebec).
Figure 18B:
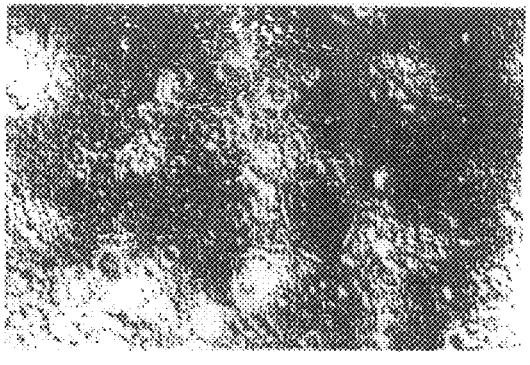
Figure 18C:
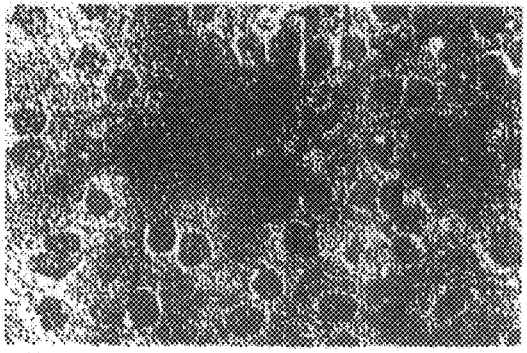
Figure 18D:
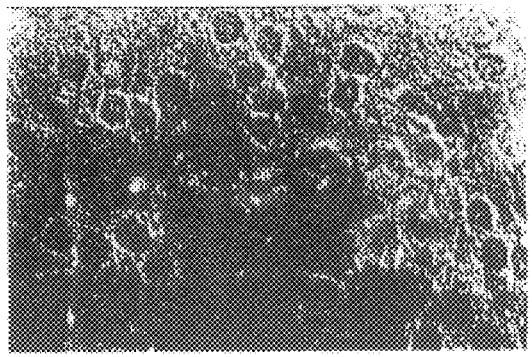

To further demonstrate the effect of the representative modulating agent N-Ac-CHAVC-NH$_2$ (SEQ ID NO:10) on tumor blood vessels, sections of the tumors described above were stained for Von Willebrand Factor VIII, a blood vessel-specific marker. An untreated tumor is shown in FIG. 16, and a treated tumor section is shown in FIG. 17. Taken together, these results clearly demonstrate that the representative modulating agent is capable of damaging tumor blood vessels and stopping tumor growth in vivo.

EXAMPLE 9

Disruption of Angiogenesis

Blood vessels are composed of adherent endothelial cells. This Example illustrates the use of a representative cyclic peptide to block angiogenesis (the growth of blood vessels from pre-existing blood vessels).

The chick chorioallantoic membrane assay was used to assess the effects of cyclic peptides on angiogenesis (Iruela-Arispe et al., *Molecular Biology of the Cell* 6:327–343, 1995). Cyclic peptides were embedded in a mesh composed of vitrogen at concentrations of 3, 17, and 33 µg/mesh. The meshes were then applied to 12-day-old chick embryonic chorioallantoic membranes. After 24 hours, the effects of the peptides on angiogenesis were assessed by computer assisted morphometric analysis.

The ability of representative cyclic peptides to inhibit angiogenesis is illustrated by the results presented in Table 3. For each concentration of cyclic peptide, the percent inhibition of angiogenesis (relative to the level of angiogenesis in the absence of cyclic peptide) is provided. Assays were performed in the presence (+) or absence (−) of 0.01 mM VEGF. For example, the cyclic peptide N-Ac-CHAVC-NH$_2$ (SEQ ID NO:10) inhibited angiogenesis by 46%, 51%, and 51% at concentrations of 3, 17, and 33 µg/mesh, respectively. The N-cadherin selective peptides N-Ac-CAHAVDIC-NH$_2$ (SEQ ID NO:18) and N-Ac-CAHAVDC-NH$_2$ (SEQ ID NO:19) also inhibited angiogenesis significantly. The E-cadherin selective cyclic peptides N-Ac-CHAVSC-NH$_2$ (SEQ ID NO:25) and N-Ac-CSHAVSSC-NH$_2$ (SEQ ID NO:27), as well as the scrambled peptide N-Ac-CVAHC-NH$_2$ (SEQ ID NO:15), were found to be relatively inactive in this assay.

TABLE 3

| Compound | Concentration, μg/mesh ±VEGF | | | | | |
|---|---|---|---|---|---|---|
| | 3(−) | 3(+) | 17(−) | 17(+) | 33(−) | 33(+) |
| H-CHAVC-NH$_2$ (SEQ ID NO:10) | 11% | 27% | 13% | 34% | 17% | 35% |
| N-Ac-CHAVSC-NH$_2$ (SEQ ID NO:25) | 11% | 17% | 12% | 16% | 17% | 19% |
| N-Ac-CVAHC-NH$_2$ (SEQ ID NO:15) | −1% | 7% | 13% | 24% | 12% | 25% |
| N-Ac-CHAVC-NH$_2$ (SEQ ID NO:10) | 12% | 46% | 22% | 51% | 28% | 51% |
| N-Ac-CAHAVDIC-NH$_2$ (SEQ ID NO:18) | −1% | 21% | 15% | 37% | 33% | 49% |
| N-Ac-CAHAVDC-NH$_2$ (SEQ ID NO:19) | 21% | 59% | 27% | 72% | 31% | 79% |
| N-Ac-CSHAVSSC-NH$_2$ (SEQ ID NO:27) | 1% | −3% | −3% | +12% | 17% | 7% |

EXAMPLE 10

Induction of Apoptosis in Cancer Cells

This Example illustrates the use of a representative modulating agent for killing human ovarian cancer cells.

SKOV3 human ovarian cancer cells cultured in the presence of either N-Ac-CHAVC-NH$_2$ (SEQ ID NO:10) or a control peptide (N-Ac-CHGVC-NH$_2$; SEQ ID NO:11) in MEM with 10% FBS were plated onto poly-L-lysine coated glass slides. The cells were cultured for 24 or 48 hours and fixed with 4% paraformaldehyde for 30 minutes at room temperature. The slides were then washed three times with PBS and assessed for cell death. Cells were treated with 0.5 or 0.25 mg/mL of N-Ac-CHAVC-NH$_2$ (SEQ ID NO:10) or the control N-Ac-CHGVC-NH$_2$ (SEQ ID NO:11), as indicated. Cell death was measured as described by Gavrieli et al, *J. Cell. Biol.* 119:493–501, 1992 and using the In situ cell death detection kit (Boehringer Mannheim; Laval, Quebec).

Figure 19:
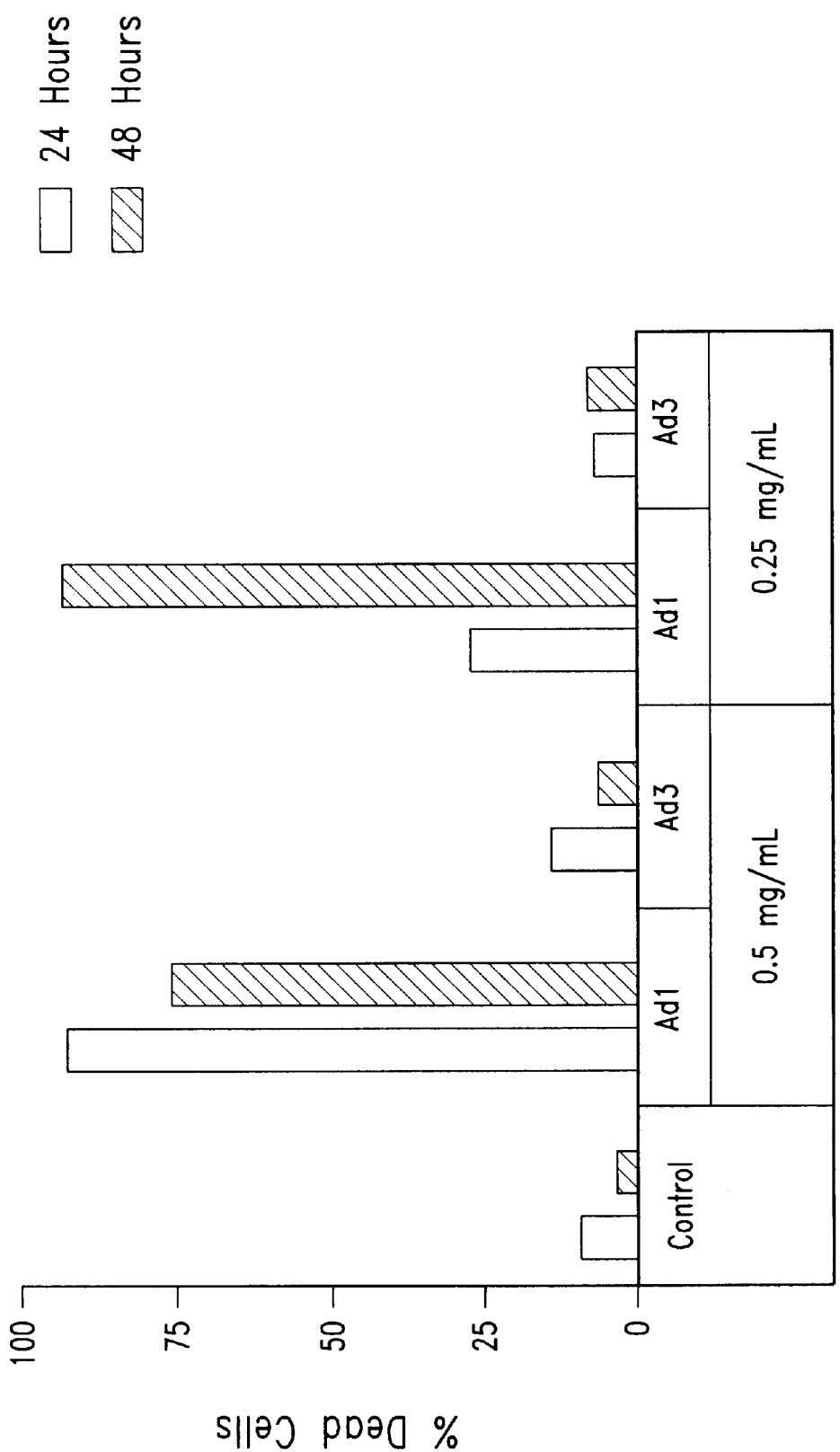
FIG. 19 is a histogram showing the percentage of dead cells following treatment with a representative cyclic peptide or a control peptide. SKOV human ovarian cancer cells containing either N-Ac-CHAVC-NH$_2$ (SEQ ID NO:10) or a control peptide (N-Ac-CHGVC-NH$_2$; SEQ ID NO:11) in MEM with 10% FBS were plated onto poly-L-lysine coated glass slides. The cells were cultured for 24 or 48 hours and fixed with 4% paraformaldehyde for 30 minutes at room temperature. The slides were then washed three times with PBS and assessed for cell death. Cells were treated with 0.5 or 0.25 mg/mL of N-Ac-CHAVC-NH$_2$ (SEQ ID NO:10) or the control N-Ac-CHGVC-NH$_2$ (SEQ ID NO:11). as indicated. Cell death was measured as described by Gavrieli et al, *J. Cell. Biol.* 119:493–501, 1992 and using the In situ cell death detection kit (Boehringer Mannheim; Laval, Quebec).

FIGS. 18A–18D show the results of such an assay, in which the cells were treated with the peptides for 48 hours. The fluorescent green nuclei evident in FIGS. 18C and 18D (cells treated with N-Ac-CHAVC-NH$_2$ (SEQ ID NO:10)) indicate that the cells are dead. In contrast, cells treated with the control peptide (FIGS. 30A and 30B) did not die. A bar graph further illustrating the ability of N-Ac-CHAVC-NH$_2$ (SEQ ID NO:10) to induce apoptosis is shown in FIG. 19. These observations indicate that this cyclic peptide can cause human ovarian cancer cell death.

From the foregoing, it will be evident that although specific embodiments of the invention have been described herein for the purpose of illustrating the invention, various modifications may be made without deviating from the spirit and scope of the invention. Accordingly, the present invention is not limited except as by the appended claims.

What is claimed is:

1. A method for treating a cancer in a mammal, comprising administering to a mammal a cell adhesion modulating agent that comprises the sequence HAV within a cyclic peptide ring, and thereby treating the cancer in the mammal.

2. A method according to claim 1, wherein the cancer is selected from the group consisting of carcinomas, leukemias and melanomas.

3. A method according to claim 1, wherein the modulating agent comprises a sequence selected from the group consisting of CHAVC (SEQ ID NO:10), CHAVDC (SEQ ID NO:16), CHAVDIC (SEQ ID NO:31), CHAVDINC (SEQ ID NO.32), CHAVDINGC (SEQ ID NO:55), CAHAVC (SEQ ID NO:17), CAHAVDC (SEQ ID NO:19), CAHAVDIC (SEQ ID NO:18), CRAHAVDC (SEQ ID NO:20), CLRAHAVC (SEQ ID NO:21), CLRAHAVDC (SEQ ID NO:22), CSHAVC (SEQ ID NO:24), CHAVSC (SEQ ID NO:25), CSHAVSC (SEQ ID NO:26), CSHAVSSC (SEQ ID NO:27), CHAVSSC (SEQ ID NO:28), KHAVD (SEQ ID NO:12), DHAVK (SEQ ID NO:13), KHAVE (SEQ ID NO:14), AHAVDI (SEQ ID NO:23), SHAVDSS (SEQ ID NO:56), KSHAVSSD (SEQ ID NO:30) and derivatives of the foregoing sequences having one or more C-terminal, N-terminal and/or side chain modifications.

4. A method according to claim 1, wherein the cyclic peptide comprises an N-terminal acetyl group.

5. A method according to claim 1, wherein the cyclic peptide comprises the sequence N-Ac-CHAVC-NH$_2$ (SEQ ID NO:10).

6. A method according to claim 1, wherein the modulating agent is present within a pharmaceutical composition comprising a pharmaceutically acceptable carrier.

7. A method according to claim 1, wherein the cell adhesion recognition sequence comprises a sequence selected from the group consisting of NQK, NRN, NKD, EKD, ERD, DDK, EEY, EAQ, IYSY (SEQ ID NO:38), TSSY (SEQ ID NO:39), VTAF (SEQ ID NO:40), VSAF (SEQ ID NO:41), RGD and LYHY (SEQ ID NO:35).

\* \* \* \* \*

UNITED STATES PATENT AND TRADEMARK OFFICE
CERTIFICATE OF CORRECTION

PATENT NO.   : 6,417,325 B1
DATED        : July 9, 2002
INVENTOR(S)  : Orest W. Blaschuk et al.

It is certified that error appears in the above-identified patent and that said Letters Patent is hereby corrected as shown below:

<u>Title page,</u>
Item [56], References Cited, front cover, should include the following reference:

-- Blaschuk et al., "Identification of a Cadherin Cell Adhesion Recognition Sequence," *Developmental Biology 139*:227-229, 1990. --.
"Blaschuk et al., reference "Identification of a Conserved Region Common to Cadherins and Influenza Strain A Hemagglutinins," *Proc. Natl. Acad. Sci. USA 76*(1): 514-517, 1979." should read -- Blaschuk et al., "Identification of a Conserved Region Common to Cadherins and Influenza Strain A Hemagglutinins," *J. Mol. Biol. 211*: 679-682, 1990. --.

<u>Column 62,</u>
Line 4, should be deleted.

Signed and Sealed this

Twenty-fifth Day of March, 2003

JAMES E. ROGAN
*Director of the United States Patent and Trademark Office*

SEQUENCE LISTING

<160> NUMBER OF SEQ ID NOS: 58

<210> SEQ ID NO 1
<211> LENGTH: 108
<212> TYPE: PRT
<213> ORGANISM: Homo sapiens

<400> SEQUENCE: 1

Asp Trp Val Ile Pro Pro Ile Asn Leu Pro Glu Asn Ser Arg Gly Pro
 1               5                  10                  15

Phe Pro Gln Glu Leu Val Arg Ile Arg Ser Asp Arg Asp Lys Asn Leu
                20                  25                  30

Ser Leu Arg Tyr Ser Val Thr Gly Pro Gly Ala Asp Gln Pro Pro Thr
            35                  40                  45

Gly Ile Phe Ile Leu Asn Pro Ile Ser Gly Gln Leu Ser Val Thr Lys
        50                  55                  60

Pro Leu Asp Arg Glu Gln Ile Ala Arg Phe His Leu Arg Ala His Ala
65                  70                  75                  80

Val Asp Ile Asn Gly Asn Gln Val Glu Asn Pro Ile Asp Ile Val Ile
                85                  90                  95

```
Asn Val Ile Asp Met Asn Asp Asn Arg Pro Glu Phe
            100                 105

<210> SEQ ID NO 2
<211> LENGTH: 108
<212> TYPE: PRT
<213> ORGANISM: Mus musculus

<400> SEQUENCE: 2

Asp Trp Val Ile Pro Pro Ile Asn Leu Pro Glu Asn Ser Arg Gly Pro
 1               5                  10                  15

Phe Pro Gln Glu Leu Val Arg Ile Arg Ser Asp Arg Asp Lys Asn Leu
                20                  25                  30

Ser Leu Arg Tyr Ser Val Thr Gly Pro Gly Ala Asp Gln Pro Pro Thr
            35                  40                  45

Gly Ile Phe Ile Ile Asn Pro Ile Ser Gly Gln Leu Ser Val Thr Lys
        50                  55                  60

Pro Leu Asp Arg Glu Leu Ile Ala Arg Phe His Leu Arg Ala His Ala
 65                  70                  75                  80

Val Asp Ile Asn Gly Asn Gln Val Glu Asn Pro Ile Asp Ile Val Ile
                85                  90                  95

Asn Val Ile Asp Met Asn Asp Asn Arg Pro Glu Phe
            100                 105

<210> SEQ ID NO 3
<211> LENGTH: 108
<212> TYPE: PRT
<213> ORGANISM: Bos taurus

<400> SEQUENCE: 3

Asp Trp Val Ile Pro Pro Ile Asn Leu Pro Glu Asn Ser Arg Gly Pro
 1               5                  10                  15

Phe Pro Gln Glu Leu Val Arg Ile Arg Ser Asp Arg Asp Lys Asn Leu
                20                  25                  30

Ser Leu Arg Tyr Ser Val Thr Gly Pro Gly Ala Asp Gln Pro Pro Thr
            35                  40                  45

Gly Ile Phe Ile Ile Asn Pro Ile Ser Gly Gln Leu Ser Val Thr Lys
        50                  55                  60

Pro Leu Asp Arg Glu Leu Ile Ala Arg Phe His Leu Arg Ala His Ala
 65                  70                  75                  80

Val Asp Ile Asn Gly Asn Gln Val Glu Asn Pro Ile Asp Ile Val Ile
                85                  90                  95

Asn Val Ile Asp Met Asn Asp Asn Arg Pro Glu Phe
            100                 105

<210> SEQ ID NO 4
<211> LENGTH: 108
<212> TYPE: PRT
<213> ORGANISM: Homo sapiens

<400> SEQUENCE: 4

Asp Trp Val Val Ala Pro Ile Ser Val Pro Glu Asn Gly Lys Gly Pro
 1               5                  10                  15

Phe Pro Gln Arg Leu Asn Gln Leu Lys Ser Asn Lys Asp Arg Asp Thr
                20                  25                  30

Lys Ile Phe Tyr Ser Ile Thr Gly Pro Gly Ala Asp Ser Pro Pro Glu
            35                  40                  45

Gly Val Phe Ala Val Glu Lys Glu Thr Gly Trp Leu Leu Leu Asn Lys
```

```
            50                  55                  60
Pro Leu Asp Arg Glu Glu Ile Ala Lys Tyr Glu Leu Phe Gly His Ala
 65                  70                  75                  80

Val Ser Glu Asn Gly Ala Ser Val Glu Asp Pro Met Asn Ile Ser Ile
                 85                  90                  95

Ile Val Thr Asp Gln Asn Asp His Lys Pro Lys Phe
            100                 105
```

<210> SEQ ID NO 5
<211> LENGTH: 108
<212> TYPE: PRT
<213> ORGANISM: Mus musculus

<400> SEQUENCE: 5

```
Glu Trp Val Met Pro Ile Phe Val Pro Glu Asn Gly Lys Gly Pro
 1               5                  10                  15

Phe Pro Gln Arg Leu Asn Gln Leu Lys Ser Asn Lys Asp Arg Gly Thr
                20                  25                  30

Lys Ile Phe Tyr Ser Ile Thr Gly Pro Gly Ala Asp Ser Pro Pro Glu
            35                  40                  45

Gly Val Phe Thr Ile Glu Lys Glu Ser Gly Trp Leu Leu Leu His Met
 50                  55                  60

Pro Leu Asp Arg Glu Lys Ile Val Lys Tyr Glu Leu Tyr Gly His Ala
 65                  70                  75                  80

Val Ser Glu Asn Gly Ala Ser Val Glu Glu Pro Met Asn Ile Ser Ile
                 85                  90                  95

Ile Val Thr Asp Gln Asn Asp Asn Lys Pro Lys Phe
            100                 105
```

<210> SEQ ID NO 6
<211> LENGTH: 108
<212> TYPE: PRT
<213> ORGANISM: Homo sapiens

<400> SEQUENCE: 6

```
Asp Trp Val Ile Pro Pro Ile Ser Cys Pro Glu Asn Glu Lys Gly Pro
 1               5                  10                  15

Phe Pro Lys Asn Leu Val Gln Ile Lys Ser Asn Lys Asp Lys Glu Gly
                20                  25                  30

Lys Val Phe Tyr Ser Ile Thr Gly Gln Gly Ala Asp Thr Pro Pro Val
            35                  40                  45

Gly Val Phe Ile Ile Glu Arg Glu Thr Gly Trp Leu Lys Val Thr Glu
 50                  55                  60

Pro Leu Asp Arg Glu Arg Ile Ala Thr Tyr Thr Leu Phe Ser His Ala
 65                  70                  75                  80

Val Ser Ser Asn Gly Asn Ala Val Glu Asp Pro Met Glu Ile Leu Ile
                 85                  90                  95

Thr Val Thr Asp Gln Asn Asp Asn Lys Pro Glu Phe
            100                 105
```

<210> SEQ ID NO 7
<211> LENGTH: 108
<212> TYPE: PRT
<213> ORGANISM: Mus musculus

<400> SEQUENCE: 7

```
Asp Trp Val Ile Pro Pro Ile Ser Cys Pro Glu Asn Glu Lys Gly Glu
 1               5                  10                  15
```

```
Phe Pro Lys Asn Leu Val Gln Ile Lys Ser Asn Arg Asp Lys Glu Thr
            20                  25                  30

Lys Val Phe Tyr Ser Ile Thr Gly Gln Gly Ala Asp Lys Pro Pro Val
        35                  40                  45

Gly Val Phe Ile Ile Glu Arg Glu Thr Gly Trp Leu Lys Val Thr Gln
        50                  55                  60

Pro Leu Asp Arg Glu Ala Ile Ala Lys Tyr Ile Leu Tyr Ser His Ala
65                  70                  75                  80

Val Ser Ser Asn Gly Glu Ala Val Glu Asp Pro Met Glu Ile Val Ile
                85                  90                  95

Thr Val Thr Asp Gln Asn Asp Asn Arg Pro Glu Phe
            100                 105

<210> SEQ ID NO 8
<211> LENGTH: 5
<212> TYPE: PRT
<213> ORGANISM: Unknown
<220> FEATURE:
<221> NAME/KEY: MOD_RES
<222> LOCATION: (2)
<223> OTHER INFORMATION: Where Xaa is any amino acid
<220> FEATURE:
<223> OTHER INFORMATION: Description of Unknown Organism: Cadherin
      Calcium Binding Motif

<400> SEQUENCE: 8

Asp Xaa Asn Asp Asn
 1               5

<210> SEQ ID NO 9
<211> LENGTH: 4
<212> TYPE: PRT
<213> ORGANISM: Unknown
<220> FEATURE:
<223> OTHER INFORMATION: Description of Unknown Organism: Cadherin
      Calcium Binding Motif

<400> SEQUENCE: 9

Leu Asp Arg Glu
 1

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Cyclic
      Peptide with Classical Cell Adhesion Recognition Sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 10

Cys His Ala Val Cys
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Cyclic
      control peptide
<220> FEATURE:
```

-continued

```
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 11

Cys His Gly Val Cys
 1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with cadherin cell adhesion recognition
      sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 12

Lys His Ala Val Asp
 1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with cadherin cell adhesion recognition
      sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 13

Asp His Ala Val Lys
 1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 14

Lys His Ala Val Glu
 1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
```

```
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 15

Cys Val Ala His Cys
 1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 16

Cys His Ala Val Asp Cys
 1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 17

Cys Ala His Ala Val Cys
 1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 18

Cys Ala His Ala Val Asp Ile Cys
 1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
```

```
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 19

Cys Ala His Ala Val Asp Cys
 1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 20

Cys Arg Ala His Ala Val Asp Cys
 1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 21

Cys Leu Arg Ala His Ala Val Cys
 1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 22

Cys Leu Arg Ala His Ala Val Asp Cys
 1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence:  Cyclic
```

```
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 23

Ala His Ala Val Asp Ile
 1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 24

Cys Ser His Ala Val Cys
 1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 25

Cys His Ala Val Ser Cys
 1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 26

Cys Ser His Ala Val Ser Cys
 1               5

<210> SEQ ID NO 27
<211> LENGTH: 8
<212> TYPE: PRT
<213> ORGANISM: Artificial Sequence
<220> FEATURE:
```

```
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 27

Cys Ser His Ala Val Ser Ser Cys
  1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 28

Cys His Ala Val Ser Ser Cys
  1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 29

Ser His Ala Val Ser Ser
  1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 30

Lys Ser His Ala Val Ser Ser Asp
  1               5

<210> SEQ ID NO 31
<211> LENGTH: 7
<212> TYPE: PRT
<213> ORGANISM: Artificial Sequence
```

```
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 31

Cys His Ala Val Asp Ile Cys
  1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 32

Cys His Ala Val Asp Ile Asn Cys
  1               5

<210> SEQ ID NO 33
<211> LENGTH: 5
<212> TYPE: PRT
<213> ORGANISM: Unknown
<220> FEATURE:
<223> OTHER INFORMATION: Description of Unknown Organism:  Cadherin
      cell adhesion recognition sequencebound by
      alpha-6-beta-1 integrin

<400> SEQUENCE: 33

Tyr Ile Gly Ser Arg
  1               5

<210> SEQ ID NO 34
<211> LENGTH: 10
<212> TYPE: PRT
<213> ORGANISM: Unknown
<220> FEATURE:
<223> OTHER INFORMATION: Description of Unknown Organism:  Cadherin
      cell adhesion recognition sequence bound by N-CAM

<400> SEQUENCE: 34

Lys Tyr Ser Phe Asn Tyr Asp Gly Ser Glu
  1               5                  10

<210> SEQ ID NO 35
<211> LENGTH: 4
<212> TYPE: PRT
<213> ORGANISM: Unknown
<220> FEATURE:
<223> OTHER INFORMATION: Description of Unknown Organism:  Occluding
      cell adhesion recognition sequence

<400> SEQUENCE: 35

Leu Tyr His Tyr
  1
```

```
<210> SEQ ID NO 36
<211> LENGTH: 8
<212> TYPE: PRT
<213> ORGANISM: Unknown
<220> FEATURE:
<223> OTHER INFORMATION: Description of Unknown Organism: Claudin
      cell adhesion recognition sequence
<220> FEATURE:
<221> NAME/KEY: MOD_RES
<222> LOCATION: (2)
<223> OTHER INFORMATION: Where Xaa is either Lysine or arginine
<220> FEATURE:
<221> NAME/KEY: MOD_RES
<222> LOCATION: (3)..(4)
<223> OTHER INFORMATION: Where Xaa is an independently selected amino
      acid residue
<220> FEATURE:
<221> NAME/KEY: MOD_RES
<222> LOCATION: (5)
<223> OTHER INFORMATION: Where Xaa is either Serine or Alanine
<220> FEATURE:
<221> NAME/KEY: MOD_RES
<222> LOCATION: (6)
<223> OTHER INFORMATION: Where Xaa is either Tyrosine or Phenylalanine
<220> FEATURE:
<221> NAME/KEY: MOD_RES
<222> LOCATION: (7)
<223> OTHER INFORMATION: Where Xaa is an independently selected amino
      acid residue

<400> SEQUENCE: 36

Trp Xaa Xaa Xaa Xaa Xaa Xaa Gly
 1               5

<210> SEQ ID NO 37
<211> LENGTH: 9
<212> TYPE: PRT
<213> ORGANISM: Unknown
<220> FEATURE:
<223> OTHER INFORMATION: Description of Unknown Organism: Nonclassical
      cadherin cell adhesion recognition sequence
<220> FEATURE:
<221> NAME/KEY: MOD_RES
<222> LOCATION: (1)
<223> OTHER INFORMATION: Where Xaa is an independently selected amino
      acid residue
<220> FEATURE:
<221> NAME/KEY: MOD_RES
<222> LOCATION: (3)
<223> OTHER INFORMATION: Where Xaa is an independently selected amino
      acid residue
<220> FEATURE:
<221> NAME/KEY: MOD_RES
<222> LOCATION: (4)
<223> OTHER INFORMATION: Where Xaa is Isoleucine, Leucine or Valine
<220> FEATURE:
<221> NAME/KEY: MOD_RES
<222> LOCATION: (5)
<223> OTHER INFORMATION: Where Xaa is Aspartic Acid, Asparagine or
      Glutamic Acid
<220> FEATURE:
<221> NAME/KEY: MOD_RES
<222> LOCATION: (6)..(7)
<223> OTHER INFORMATION: Where Xaa is an independently selected amino
      acid residue
<220> FEATURE:
<221> NAME/KEY: MOD_RES
<222> LOCATION: (8)
<223> OTHER INFORMATION: Where Xaa is Serine, Threonine or Asparagine

<400> SEQUENCE: 37

Xaa Phe Xaa Xaa Xaa Xaa Xaa Xaa Gly
 1               5

<210> SEQ ID NO 38
```

```
<211> LENGTH: 4
<212> TYPE: PRT
<213> ORGANISM: Unknown
<220> FEATURE:
<223> OTHER INFORMATION: Description of Unknown Organism:
      Representative claudin cell adhesion recognition sequence

<400> SEQUENCE: 38

Ile Tyr Ser Tyr
 1

<210> SEQ ID NO 39
<211> LENGTH: 4
<212> TYPE: PRT
<213> ORGANISM: Unknown
<220> FEATURE:
<223> OTHER INFORMATION: Description of Unknown Organism:
      Representative claudin cell adhesion recognition sequence

<400> SEQUENCE: 39

Thr Ser Ser Tyr
 1

<210> SEQ ID NO 40
<211> LENGTH: 4
<212> TYPE: PRT
<213> ORGANISM: Unknown
<220> FEATURE:
<223> OTHER INFORMATION: Description of Unknown Organism:
      Representative claudin cell adhesion recognition sequence

<400> SEQUENCE: 40

Val Thr Ala Phe
 1

<210> SEQ ID NO 41
<211> LENGTH: 4
<212> TYPE: PRT
<213> ORGANISM: Unknown
<220> FEATURE:
<223> OTHER INFORMATION: Description of Unknown Organism:
      Representative claudin cell adhesion recognition sequence

<400> SEQUENCE: 41

Val Ser Ala Phe
 1

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence:
      Synthesized Cyclic Peptide
<220> FEATURE:
<221> NAME/KEY: MOD_RES
<222> LOCATION: (1)
<223> OTHER INFORMATION: 9-fluorenylmethoxycarbonyl protecting group
<220> FEATURE:
<221> NAME/KEY: MOD_RES
<222> LOCATION: (2)
<223> OTHER INFORMATION: tert-butyl protecting group
<220> FEATURE:
<221> NAME/KEY: MOD_RES
<222> LOCATION: (4)
<223> OTHER INFORMATION: tert-butyl protecting group
<220> FEATURE:
<221> NAME/KEY: MOD_RES
<222> LOCATION: (6)
<223> OTHER INFORMATION: t-butoxycarbonyl protecting group
<220> FEATURE:
```

```
<221> NAME/KEY: MOD_RES
<222> LOCATION: (7)
<223> OTHER INFORMATION: tert-butyl protecting group
<220> FEATURE:
<221> NAME/KEY: MOD_RES
<222> LOCATION: (9)
<223> OTHER INFORMATION: tert-butyl protecting group
<220> FEATURE:
<221> NAME/KEY: MOD_RES
<222> LOCATION: (10)
<223> OTHER INFORMATION: Methoxy terminal group

<400> SEQUENCE: 42

Cys Asp Gly Tyr Pro Lys Asp Cys Lys Gly
 1               5                  10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence:
      Synthesized peptide
<220> FEATURE:
<221> NAME/KEY: MOD_RES
<222> LOCATION: (1)
<223> OTHER INFORMATION: Residue has t-butoxycarbonyl, and Trityl or
      Acetamidomethyl protecting groups
<220> FEATURE:
<221> NAME/KEY: MOD_RES
<222> LOCATION: (5)..(6)
<223> OTHER INFORMATION: tert-butyl protecting group
<220> FEATURE:
<221> NAME/KEY: MOD_RES
<222> LOCATION: (7)
<223> OTHER INFORMATION: Trityl or acetaminomethly protecting group

<400> SEQUENCE: 43

Cys Gly Asn Leu Ser Thr Cys Met Leu Gly
 1               5                  10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence:
      Synthesized cyclic peptide
<220> FEATURE:
<221> NAME/KEY: MOD_RES
<222> LOCATION: (1)
<223> OTHER INFORMATION: t-butoxycarbonyl protecting group
<220> FEATURE:
<221> NAME/KEY: MOD_RES
<222> LOCATION: (5)..(6)
<223> OTHER INFORMATION: tert-butyl protecting group

<400> SEQUENCE: 44

Cys Gly Asn Leu Ser Thr Cys Met Leu Gly
 1               5                  10

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence:
      Synthesized peptide
<220> FEATURE:
<221> NAME/KEY: MOD_RES
<222> LOCATION: (2)
<223> OTHER INFORMATION: Residue has Acetamidomethyl or
      tert-Acetaminomethyl or tert-butyl protecting
```

```
      group
<220> FEATURE:
<221> NAME/KEY: MOD_RES
<222> LOCATION: (6)
<223> OTHER INFORMATION: Residue has Acetamidomethyl,
      tert-Acetamidomethyl or tert-butyl protecting group
<220> FEATURE:
<221> NAME/KEY: MOD_RES
<222> LOCATION: (9)
<223> OTHER INFORMATION: AMIDATION

<400> SEQUENCE: 45

Cys Tyr Ile Gln Asn Cys Pro Leu Gly
  1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence:
      Synthesized cyclic peptide
<220> FEATURE:
<221> NAME/KEY: MOD_RES
<222> LOCATION: (9)
<223> OTHER INFORMATION: AMIDATION

<400> SEQUENCE: 46

Cys Tyr Ile Gln Asn Cys Pro Leu Gly
  1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group
<220> FEATURE:
<221> NAME/KEY: MOD_RES
<222> LOCATION: (5)
<223> OTHER INFORMATION: Where Xaa is beta,beta-dimethyl cysteine

<400> SEQUENCE: 47

Cys His Ala Val Xaa
  1               5

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence:  Cyclic
      Peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group
<220> FEATURE:
<221> NAME/KEY: MOD_RES
<222> LOCATION: (2)
<223> OTHER INFORMATION: Where Xaa is beta,beta-tetramethylene
      cysteine

<400> SEQUENCE: 48
```

Ile Xaa Tyr Ser His Ala Val Ser Cys Glu
 1               5                  10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Cyclic
      Peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group
<220> FEATURE:
<221> NAME/KEY: MOD_RES
<222> LOCATION: (2)
<223> OTHER INFORMATION: Where Xaa is beta,beta-pentamethylene cysteine

<400> SEQUENCE: 49

Ile Xaa Tyr Ser His Ala Val Ser Ser Cys
 1               5                  10

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group
<220> FEATURE:
<221> NAME/KEY: MOD_RES
<222> LOCATION: (1)
<223> OTHER INFORMATION: Where Xaa is beta-mercaptopropionic acid

<400> SEQUENCE: 50

Xaa Tyr Ser His Ala Val Ser Ser Cys
 1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group
<220> FEATURE:
<221> NAME/KEY: MOD_RES
<222> LOCATION: (1)
<223> OTHER INFORMATION: Where Xaa is
      beta,beta-pentamethylene-beta-mercaptopropionic
      acid

<400> SEQUENCE: 51

Xaa Tyr Ser His Ala Val Ser Ser Cys
 1               5

```
<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<221> NAME/KEY: MOD_RES
<222> LOCATION: (4)
<223> OTHER INFORMATION: Where Serine is D-Serine

<400> SEQUENCE: 52

His Ala Val Ser Ser
 1               5

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence:
      Synthesized cyclic peptide

<400> SEQUENCE: 53

Trp Gly Gly Trp
 1

<210> SEQ ID NO 54
<211> LENGTH: 15
<212> TYPE: PRT
<213> ORGANISM: Homo sapiens
<220> FEATURE:
<223> OTHER INFORMATION: Description of Artificial Sequence:
      Representative immunogen containing the HAV
      classical cadherin cell adhesion recognition
      sequence
<220> FEATURE:
<223> OTHER INFORMATION: N-cadherin with HAV cell adhesion recognition
      sequence and flanking amino acids

<400> SEQUENCE: 54

Phe His Leu Arg Ala His Ala Val Asp Ile Asn Gly Asn Gln Val
 1               5                  10                  15

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
      recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 55

Cys His Ala Val Asp Ile Asn Gly Cys
 1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence:  Cyclic
      peptide with classical cadherin cell adhesion
```

```
            recognition sequence
<220> FEATURE:
<223> OTHER INFORMATION: Cyclic Peptide may comprise N-terminal
      modification such as acetyl or alkoxybenzyl group
      and/or C-terminal modifications such as amide or
      ester group

<400> SEQUENCE: 56

Ser His Ala Val Asp Ser Ser
  1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence:  classical
      cadherin cell adhesion recognition sequence for
      junction adhesion molecule

<400> SEQUENCE: 57

Ser Phe Thr Ile Asp Pro Lys Ser Gly
  1               5

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence:
      Synthesized Peptide
<220> FEATURE:
<221> NAME/KEY: MOD_RES
<222> LOCATION: (1)
<223> OTHER INFORMATION: BLOCKED by 9-fluorenymethyloxycarbonyl
<220> FEATURE:
<221> NAME/KEY: MOD_RES
<222> LOCATION: (2)
<223> OTHER INFORMATION: tert-butyl protecting group
<220> FEATURE:
<221> NAME/KEY: MOD_RES
<222> LOCATION: (4)
<223> OTHER INFORMATION: tert-butyl protecting group
<220> FEATURE:
<221> NAME/KEY: MOD_RES
<222> LOCATION: (6)
<223> OTHER INFORMATION: t-Butoxycarbonyl protecting group
<220> FEATURE:
<221> NAME/KEY: MOD_RES
<222> LOCATION: (7)
<223> OTHER INFORMATION: tert-butyl protecting group
<220> FEATURE:
<221> NAME/KEY: MOD_RES
<222> LOCATION: (9)
<223> OTHER INFORMATION: tert-butyl protecting group
<220> FEATURE:
<221> NAME/KEY: MOD_RES
<222> LOCATION: (10)
<223> OTHER INFORMATION: Methoxy terminal group

<400> SEQUENCE: 58

Cys Asp Gly Tyr Pro Lys Asp Cys Lys Gly
  1               5                  10
```